(12) United States Patent
Huby

(10) Patent No.: US 10,821,257 B2
(45) Date of Patent: Nov. 3, 2020

(54) RESPIRATORY SYSTEM WITH HUMIDIFIER AND CONFORMABLE RESERVOIR

(71) Applicant: ResMed Pty Ltd, Bella Vista, New South Wales (AU)

(72) Inventor: Ronald James Huby, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 918 days.

(21) Appl. No.: 15/285,785

(22) Filed: Oct. 5, 2016

(65) Prior Publication Data

US 2017/0095635 A1    Apr. 6, 2017

Related U.S. Application Data

(60) Provisional application No. 62/237,206, filed on Oct. 5, 2015.

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0069* (2014.02); *A61M 16/024* (2017.08);
(Continued)

(58) Field of Classification Search
CPC ...... A61G 10/04; A61G 11/00; A61G 11/009; A61M 1/0011; A61M 1/0015; A61M 11/06; A61M 16/0066; A61M 16/06; A61M 16/08; A61M 16/0833; A61M 16/0875; A61M 16/1075; A61M 16/108; A61M 16/1085; A61M 16/109; A61M 16/1095; A61M 16/16; A61M 16/206; A61M 2205/3368; A61M 2205/3653; A61M 2205/8206; B67D 1/0004; B67D 1/07; B67D 1/0801; B67D 1/0895; B67D 1/10; B67D 2001/1259; B67D 2210/00015;
(Continued)

(56) References Cited

U.S. PATENT DOCUMENTS

| | | | | |
|---|---|---|---|---|
| 2,114,594 A | * | 4/1938 | Elliott | F24F 6/06 261/100 |
| 3,710,791 A | * | 1/1973 | Deaton | A61G 10/04 128/205.26 |

(Continued)

FOREIGN PATENT DOCUMENTS

WO    WO 2008/148154 A1    12/2008
WO    WO 2012/171072 A1    12/2012
(Continued)

*Primary Examiner* — Annette Dixon
(74) *Attorney, Agent, or Firm* — Nixon & Vanderhye P.C.

(57) ABSTRACT

A humidifier for humidifying a flow of air to be delivered to a patient includes a base unit having at least one wall defining a receiving space. The base unit also includes a variable volume reservoir configured to hold a body of water and receive the flow of air to humidify the flow of air for delivery to the patient. The receiving space is configured to receive the variable volume reservoir and the variable volume reservoir is conformable to a shape of the receiving space. The humidifier further includes a heater for heating the body of water.

40 Claims, 21 Drawing Sheets

(51) Int. Cl.
*A61M 16/20* (2006.01)
*A61M 16/06* (2006.01)
*A61M 16/00* (2006.01)

(52) U.S. Cl.
CPC ...... *A61M 16/0666* (2013.01); *A61M 16/109* (2014.02); *A61M 16/1055* (2013.01); *A61M 16/208* (2013.01); *A61M 16/0051* (2013.01); *A61M 16/0605* (2014.02); *A61M 2016/003* (2013.01); *A61M 2016/0027* (2013.01); *A61M 2016/0039* (2013.01); *A61M 2205/21* (2013.01); *A61M 2205/3365* (2013.01); *A61M 2205/3368* (2013.01); *A61M 2205/3569* (2013.01); *A61M 2205/3592* (2013.01); *A61M 2205/505* (2013.01); *A61M 2209/06* (2013.01)

(58) Field of Classification Search
CPC ......... B67D 2210/00097; B67D 3/0009; F24F 2221/12; F24F 6/04; F24F 6/06; Y10S 128/24; Y10S 128/911; Y10S 261/65
See application file for complete search history.

(56) References Cited

U.S. PATENT DOCUMENTS

| | | | | |
|---|---|---|---|---|
| 3,864,437 | A | * | 2/1975 | Blaszkowski ............. F24F 6/04 261/120 |
| 4,012,473 | A | * | 3/1977 | Lindsey ................. A61M 11/06 261/142 |
| 4,152,379 | A | * | 5/1979 | Suhr ................. A61M 16/1075 128/204.14 |
| 4,161,179 | A | * | 7/1979 | Abramson ........... A61M 1/0011 128/DIG. 24 |
| 4,399,080 | A | * | 8/1983 | Swank ...................... F24F 6/06 128/200.17 |
| 4,462,397 | A | * | 7/1984 | Suzuki .................. A61M 16/08 128/200.14 |
| 4,624,806 | A | | 11/1986 | Koszyk |
| 4,861,523 | A | | 8/1989 | Beran |
| 7,866,944 | B2 | | 1/2011 | Kenyon et al. |
| 8,459,259 | B2 | * | 6/2013 | Klasek ............. A61M 16/0066 128/203.27 |
| 8,636,479 | B2 | | 1/2014 | Kenyon et al. |
| 8,638,014 | B2 | | 1/2014 | Sears et al. |
| 8,820,322 | B1 | | 9/2014 | Gordon |
| 2015/0274500 | A1 | * | 10/2015 | Orita .................... B67D 3/0009 222/105 |

FOREIGN PATENT DOCUMENTS

| WO | WO 2013/020167 A1 | 2/2013 |
|---|---|---|
| WO | WO 2013/049660 A2 | 4/2013 |

\* cited by examiner

RESPIRATORY SYSTEM WITH HUMIDIFIER AND CONFORMABLE RESERVOIR

CROSS REFERENCE TO RELATED APPLICATIONS

This application is a non-provisional of U.S. Application No. 62/237,206, filed Oct. 5, 2015, the entire contents of which incorporated herein by reference.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use.

1.2 Description of the Related Art

1.2.1 Human Respiratory System and its Disorders

The respiratory system of the body facilitates gas exchange. The nose and mouth form the entrance to the airways of a patient.

A range of respiratory disorders exist. Examples of respiratory disorders may include (and/or may be related to) Obstructive Sleep Apnea (OSA), Cheyne-Stokes Respiration (CSR), Respiratory Insufficiency, Obesity Hyperventilation Syndrome (OHS), Chronic Obstructive Pulmonary Disease (COPD), Neuromuscular Disease (NMD) and Chest wall disorders. Certain disorders may be characterised by particular events, e.g. apneas, hypopneas, and hyperpneas.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Examples of respiratory therapies include: (i) Continuous Positive Airway Pressure (CPAP) therapy, which has been used to treat Obstructive Sleep Apnea (OSA); (ii) Non-invasive ventilation (NIV), which provides ventilatory support to a patient through the upper airways to assist the patient breathing and/or maintain adequate oxygen levels in the body by doing some or all of the work of breathing via a non-invasive patient interface; and (iii) Invasive ventilation (IV), which provides ventilatory support to patients that are no longer able to effectively breathe themselves and may be provided using a tracheostomy tube.

1.2.3 Treatment Systems

These therapies may be provided by a treatment system or device. Such systems and devices may also be used to diagnose a condition without treating it.

A treatment system may comprise a Respiratory Pressure Therapy device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, nasal pillows or cannula to the nose, a tube to the mouth or a tracheostomy tube to the trachea of a patient.

1.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings Some medical humidifiers may provide inadequate humidification, some are difficult or inconvenient to use by patients.

Medical humidifiers typically comprise a humidifier reservoir for retaining a body of water for humidifying the flow of air, and a heat source (e.g. a resistive heater) configured heat the body of water. Typically, heat is transferred from the heat source to the reservoir by conduction.

Construction and/or arrangement of the heat source and the humidifier reservoir to achieve appropriate thermal contact therebetween (and thus heat transfer) can be challenging. For example, air gaps formed between the heat source and the heat transfer target may greatly decrease thermal contact, as air is an insulating medium (i.e. not a good heat-conducting material).

In many prior art humidifiers, high precision, flat heater plates (heat source) are configured to be coupled with flat conductive plates (heat target) in a humidifier reservoir to meet thermal contact and therefore heat transfer requirements. Typically these plates are manufactured from a conductive metal (e.g. steel or aluminium) and can be costly.

Another challenge to adequate thermal contact between the heater plate and the conductive plate is that of managing manufacturing and assembly tolerances in relation to insertion and/or retention of the reservoir in the humidifier. In some prior art humidifiers, the heater plates and/or the humidifier reservoir may include a spring element to bias the heater plate and the conductive plate toward each other to improve thermal contact therebetween.

Such prior art solutions listed above may increase material and/or manufacturing costs of the humidifier for the manufacturer while potentially decreasing the manufacturing yield, which may not be desirable. Furthermore, humidifiers reservoirs are typically disposable for one or a plurality of reasons, such as wear, foreign matter build-up, regulatory and hygienic requirements, such as for multi-patient use. Thus, it is preferable for the humidifier reservoir to be a low-cost item.

1.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a flexible humidifier reservoir configured to contain a body of water for humidifying a flow of pressurized breathable gas generated by a respiratory apparatus.

Another form of the present technology comprises a kit of one or more pre-filled flexible humidifier reservoirs.

Another form of the present technology comprises a flexible humidifier reservoir configured to be coupled to more than one type of humidifier Another form of the present technology comprises a flexible humidifier reservoir that is prefilled with water for humidifying a flow of pressurized breathable gas generated by a respiratory apparatus base.

Another form of the present technology comprises a flexible humidifier reservoir configured to be coupled to more than one type of respiratory apparatus.

Another form of the present technology comprises a method for humidifying a flow of pressurized breathable gas generated by a respirator apparatus.

Another aspect of the present technology comprises a method for changing the shape of a humidifier reservoir to conform to the shape of a humidifier base or a receiving portion of a flow generator.

Another aspect of one form of the present technology is a humidifier for a continuous positive airway pressure (CPAP) apparatus. The humidifier includes a base unit configured to be coupled to the CPAP apparatus and comprising a receiving space and a variable volume chamber configured to hold a body of water and receive pressurized gas from the CPAP apparatus to humidify the pressurized gas. The receiving space is configured to receive the variable volume chamber and the variable volume chamber is conformable to a shape of the receiving space.

Another aspect of one form of the present technology is a humidifier for a continuous positive airway pressure (CPAP) apparatus. The humidifier includes a flexible chamber configured to hold a body of water and receive pressurized gas from the CPAP apparatus to humidify the pressurized gas and a base unit configured to support the flexible chamber. The flexible chamber is configured to conform to a shape of a receiving space of the base unit upon being received by the base unit.

Another aspect of one form of the present technology is a humidifier for a continuous positive airway pressure (CPAP) apparatus. The humidifier includes a conformable chamber configured to hold a body of water and receive pressurized gas from the CPAP apparatus to humidify the pressurized gas and a retaining space configured to retain the flexible chamber in a fixed position relative to the CPAP apparatus. The walls of the retaining space are configured to force the conformable chamber into a predetermined shape upon the conformable chamber being received by the retaining space.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1 shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Respiratory System and Facial Anatomy

FIG. 2 shows an overview of a human respiratory system including the nasal and oral cavities, the larynx, vocal folds, esophagus, trachea, bronchus, lung, alveolar sacs, heart and diaphragm.

3.3 Patient Interface

FIG. 3 shows a patient interface in the form of a nasal mask in accordance with one form of the present technology.

3.4 RPT Device

3.5 Humidifier

Figure 5A:
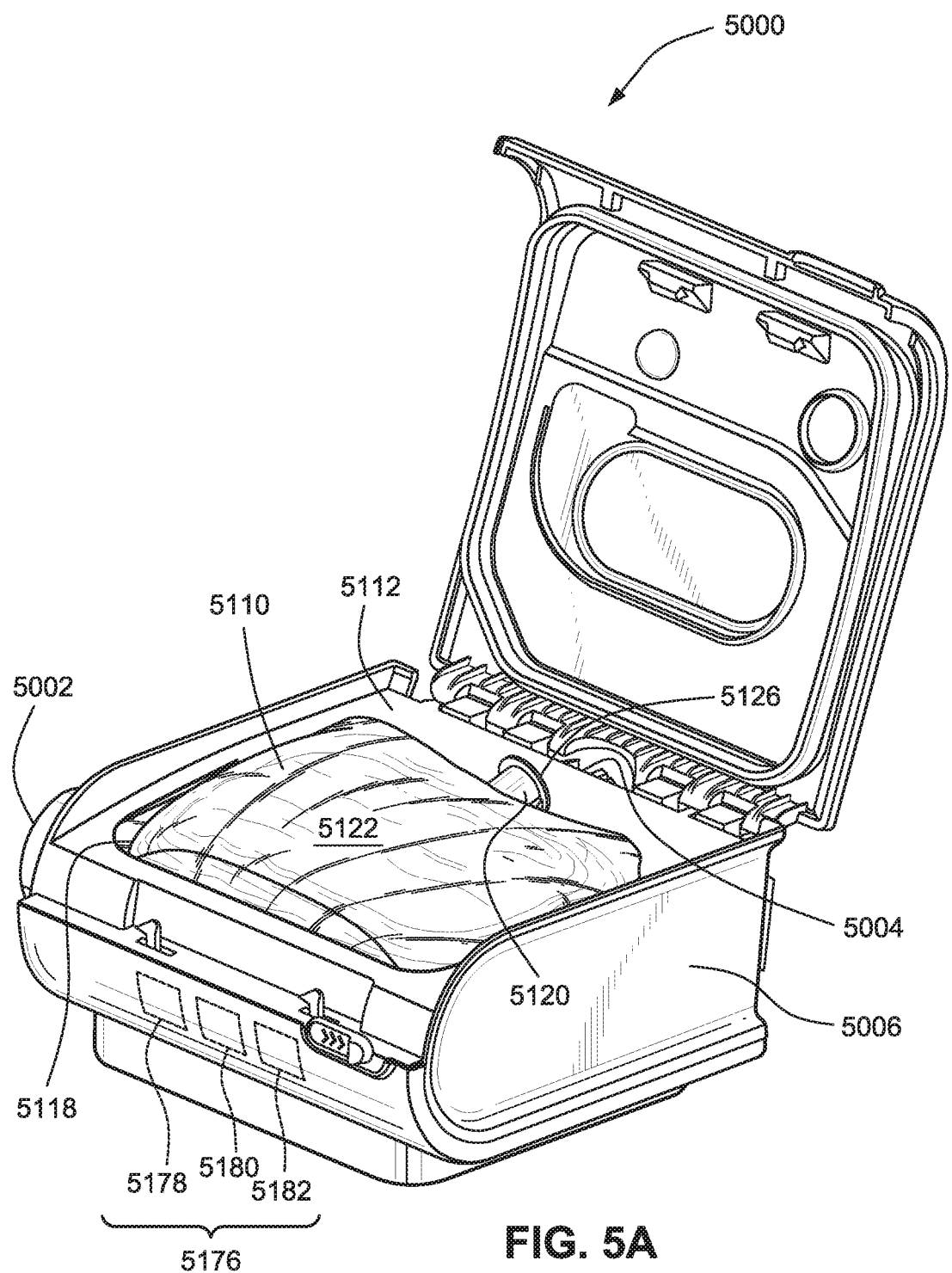

FIG. 5A shows an isometric view of a humidifier in accordance with one form of the present technology.

Figure 5B:
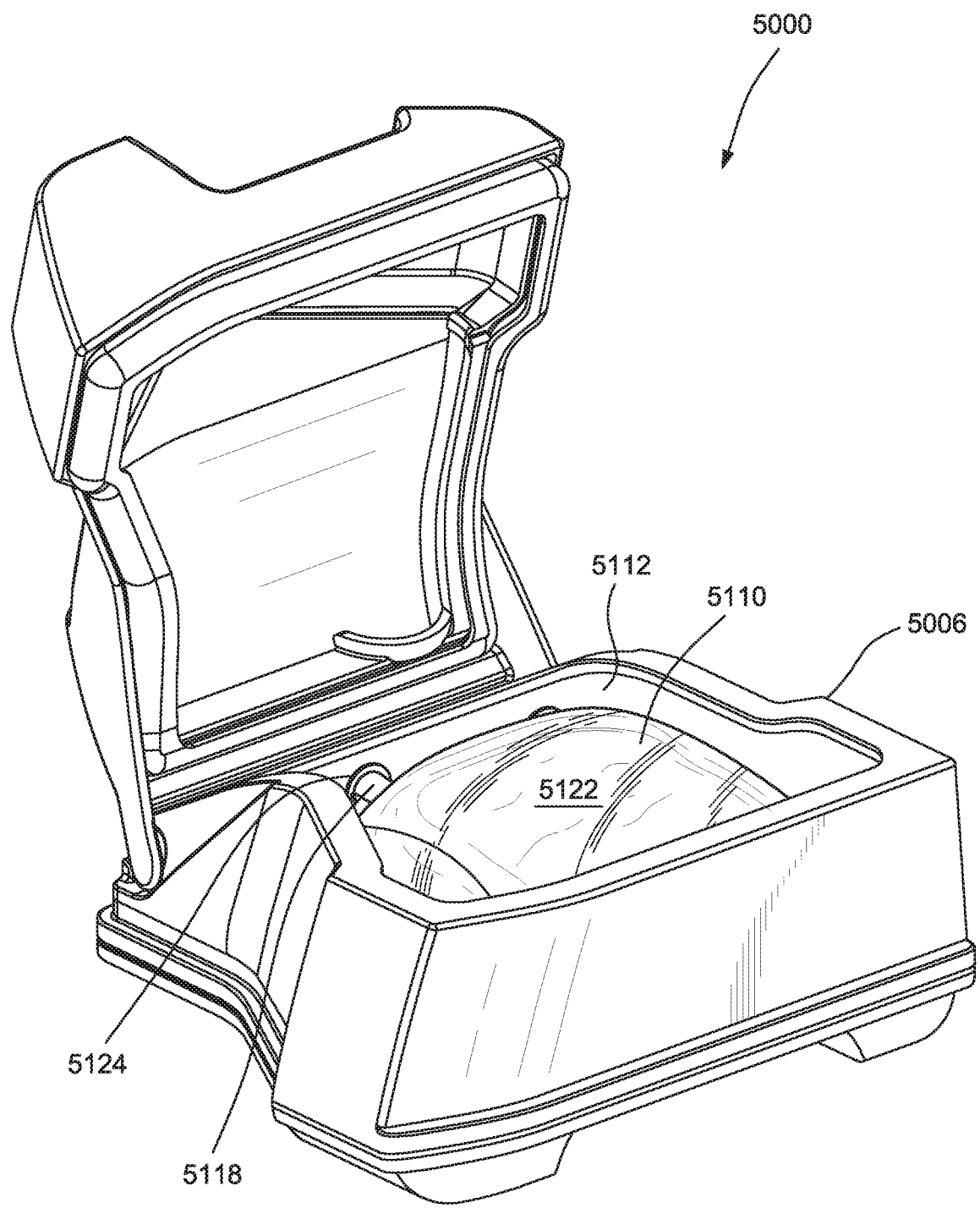

FIG. 5B shows an isometric view of a humidifier in accordance with one form of the present technology.

Figure 5C:
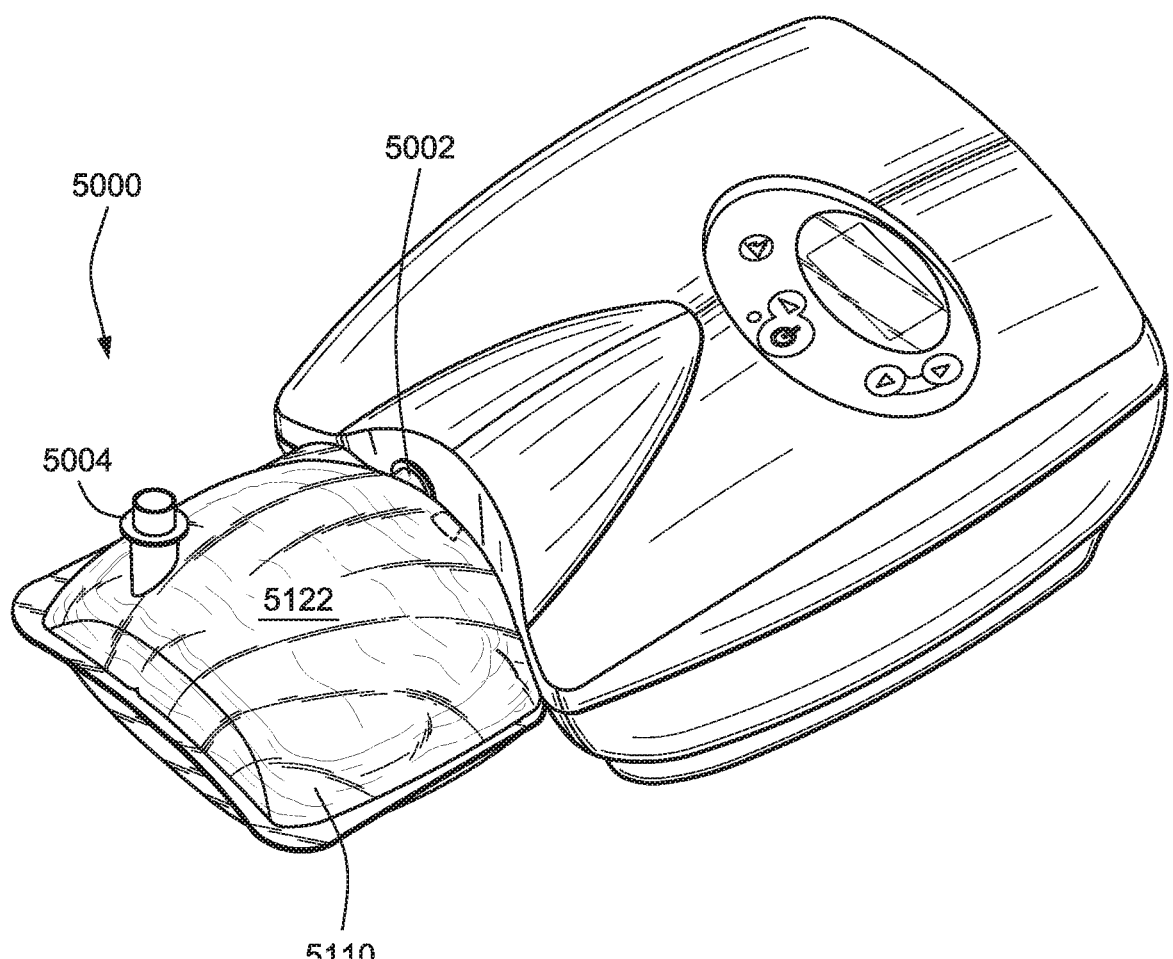

FIG. 5C shows a humidifier in accordance with one form of the present technology.

Figure 5D:
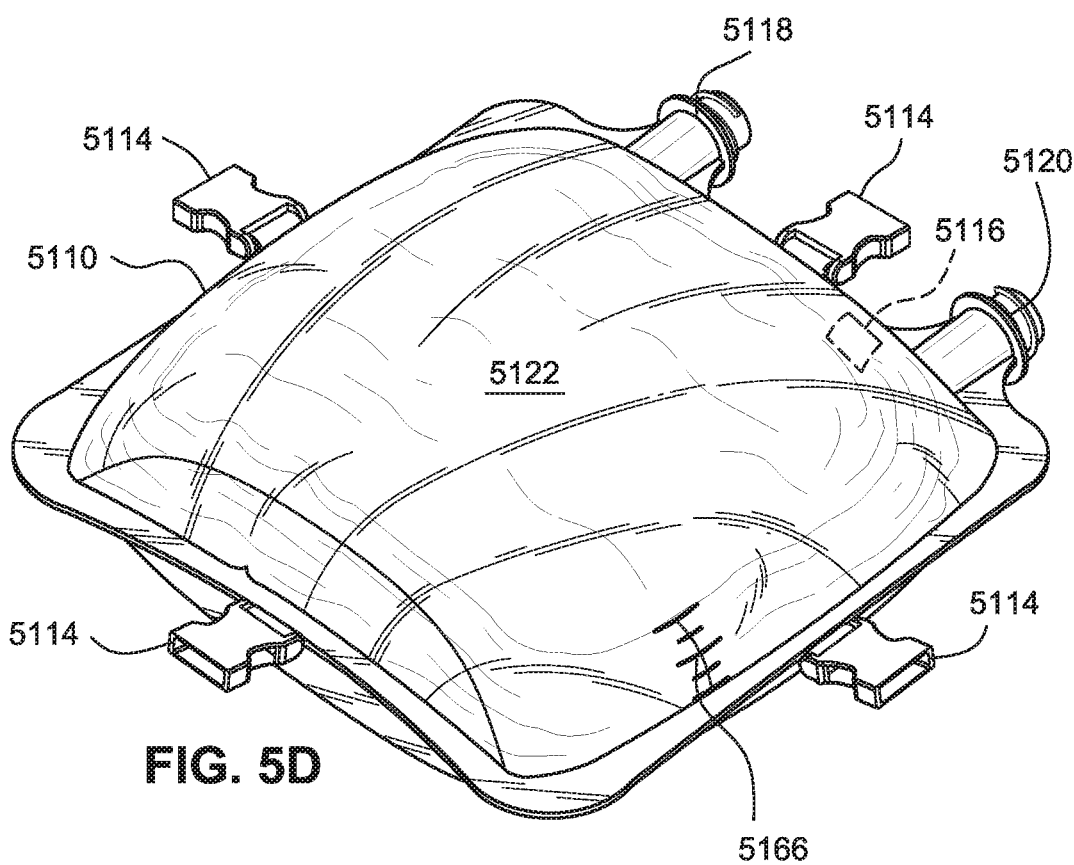

FIG. 5D shows a flexible reservoir according to one form of the present technology.

Figure 5E:
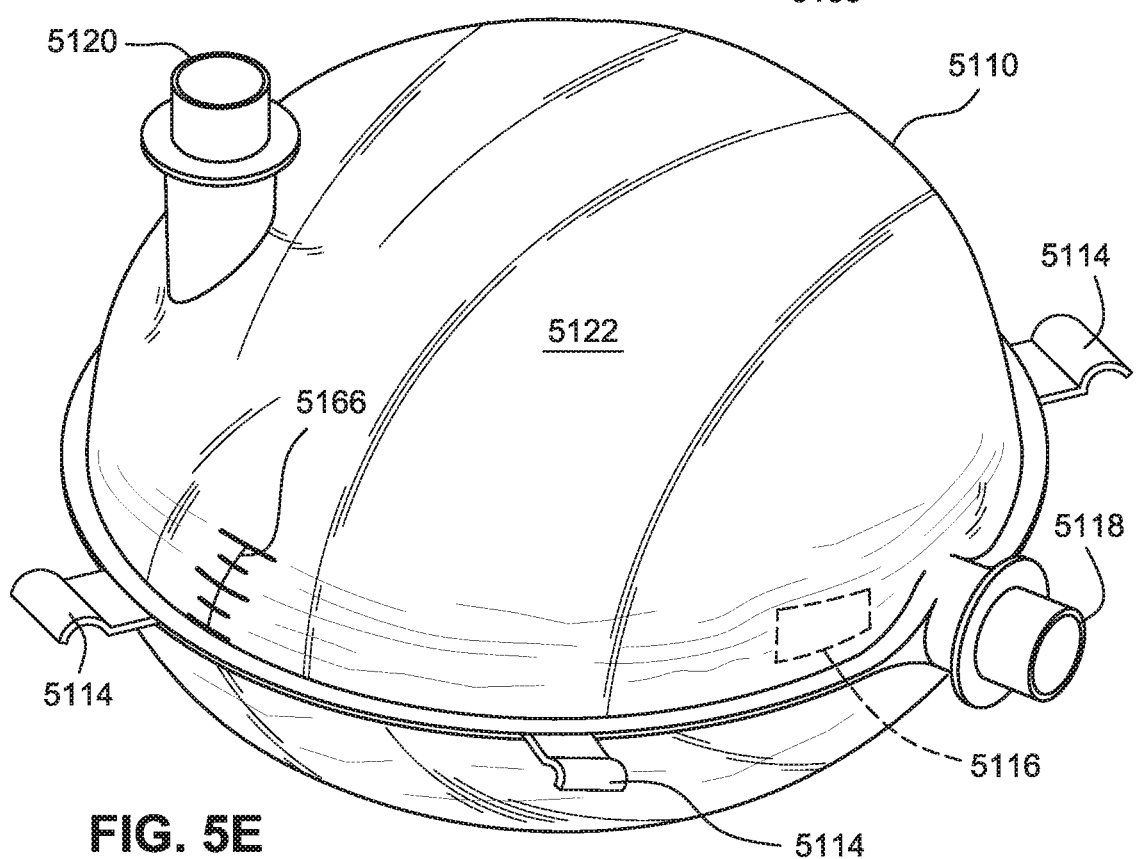

FIG. 5E shows a flexible reservoir according to one form of the present technology.

Figure 5F:
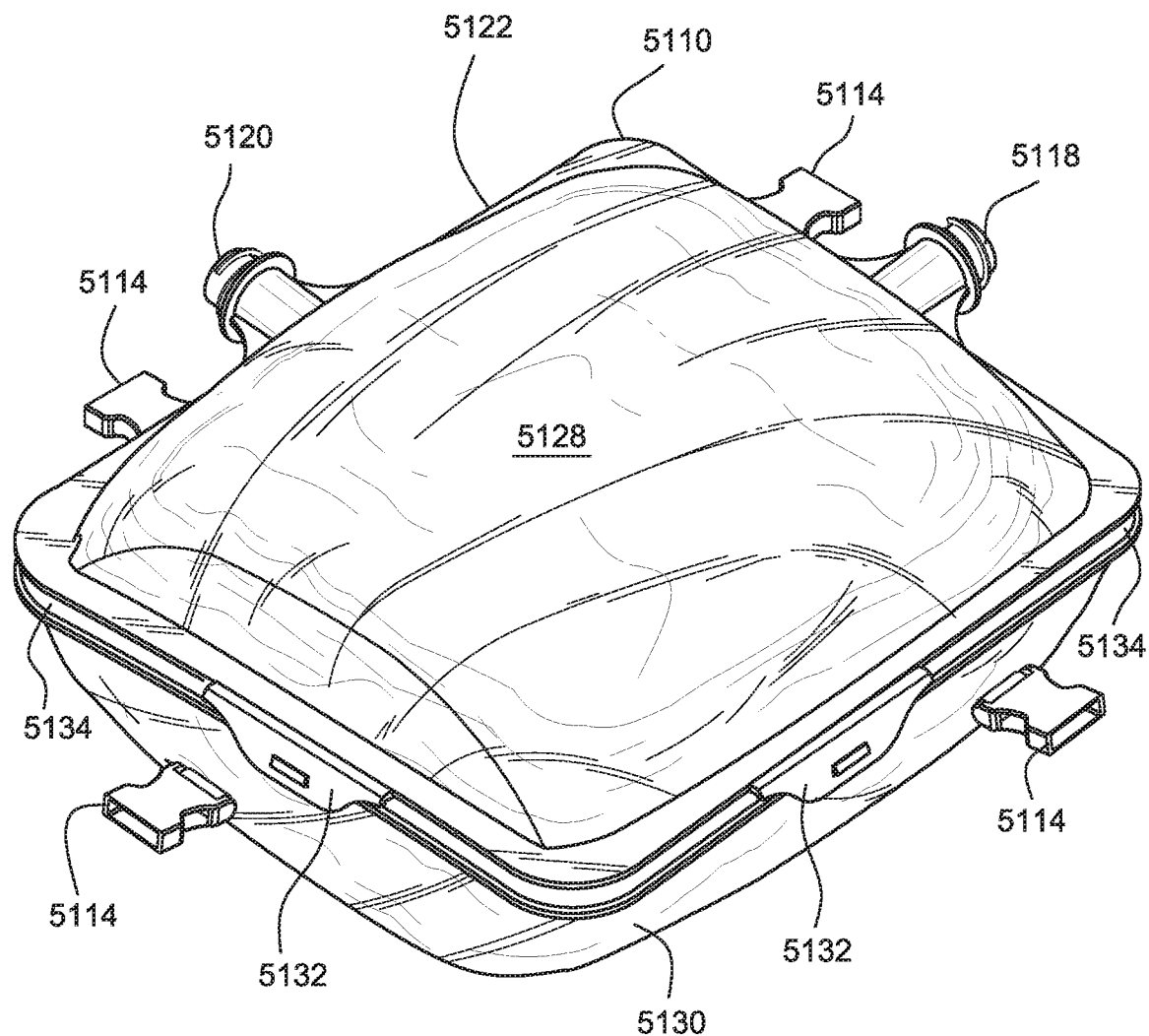

FIG. 5F shows a flexible reservoir according to one form of the present technology.

Figure 5G:
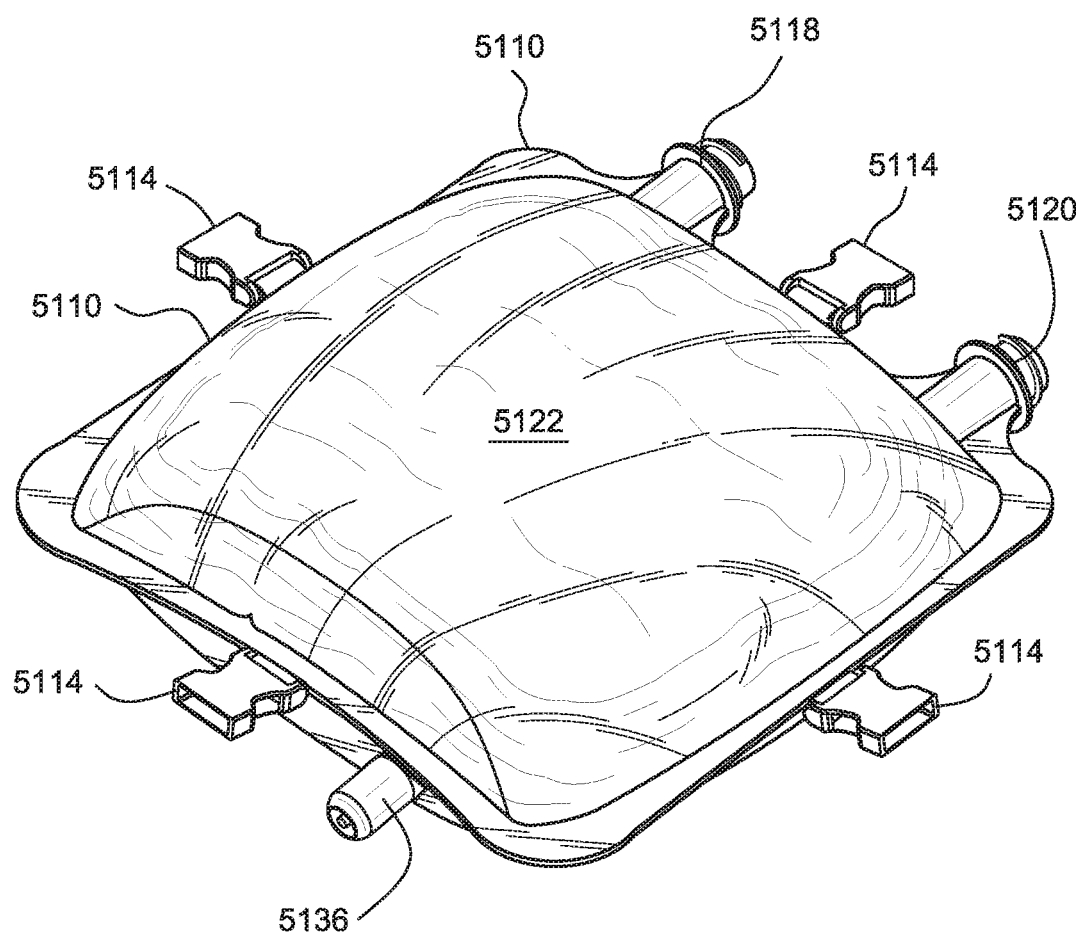

FIG. 5G shows a flexible reservoir according to one form of the present technology.

Figure 5H:
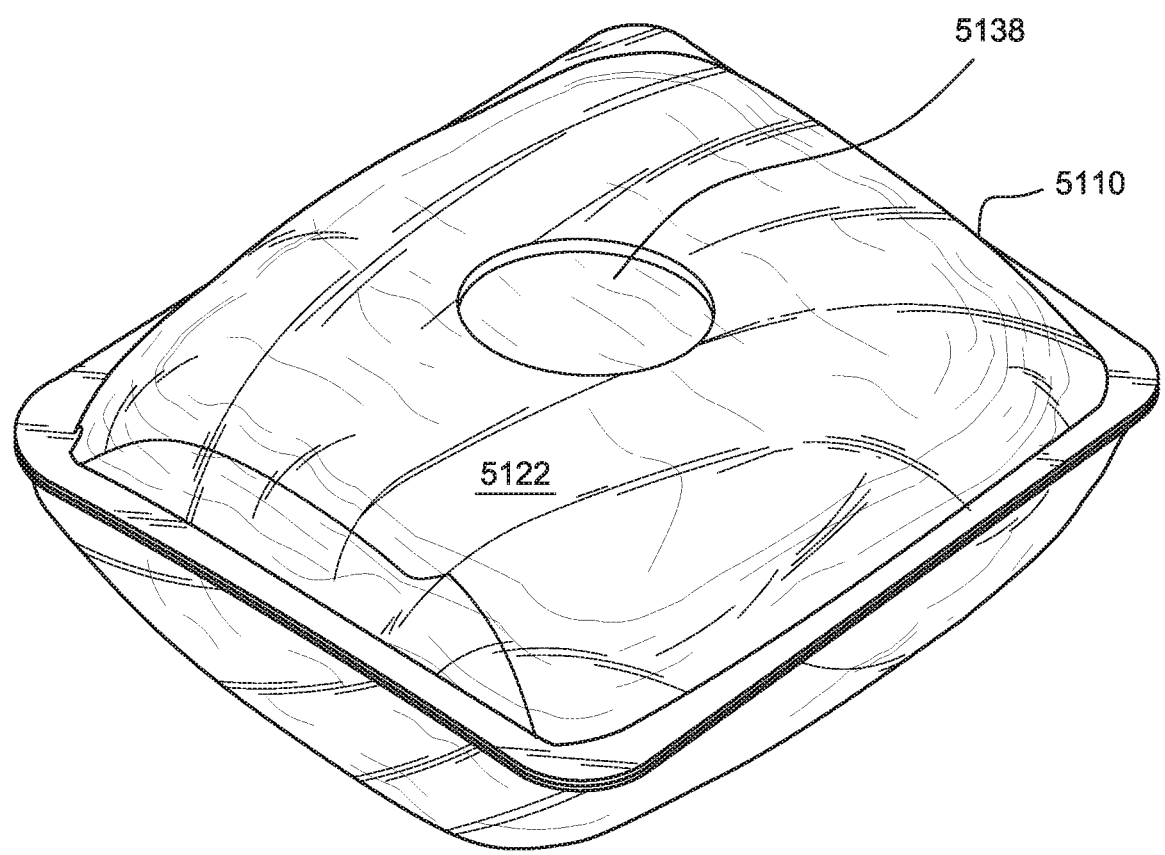

FIG. 5H shows a flexible reservoir according to one form of the present technology.

Figure 5I:
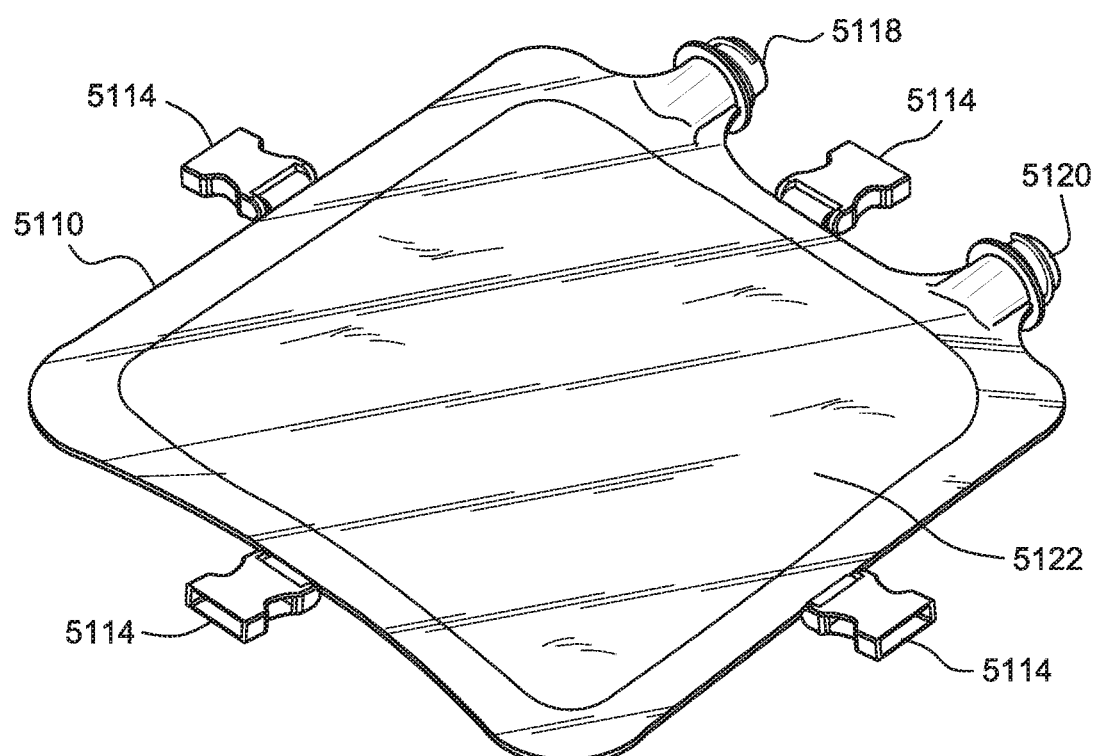

FIG. 5I shows a flexible reservoir according to one form of the present technology.

Figure 5J:
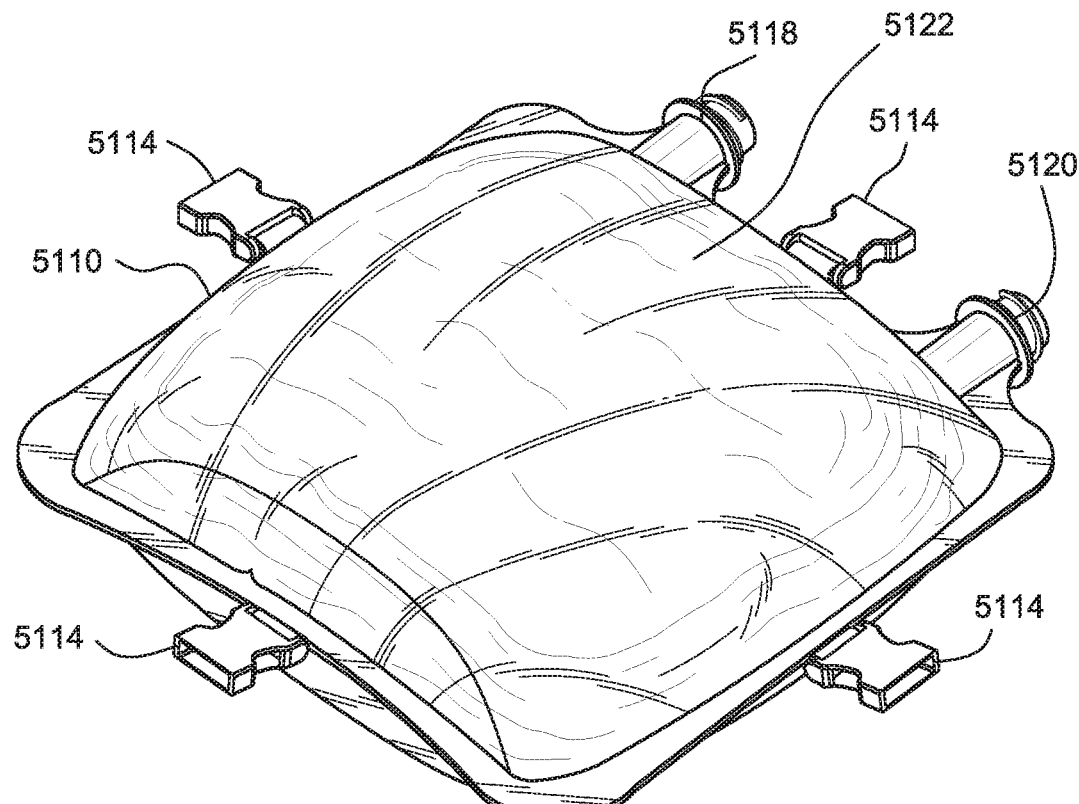

FIG. 5J shows a flexible reservoir according to one form of the present technology.

Figure 5K:
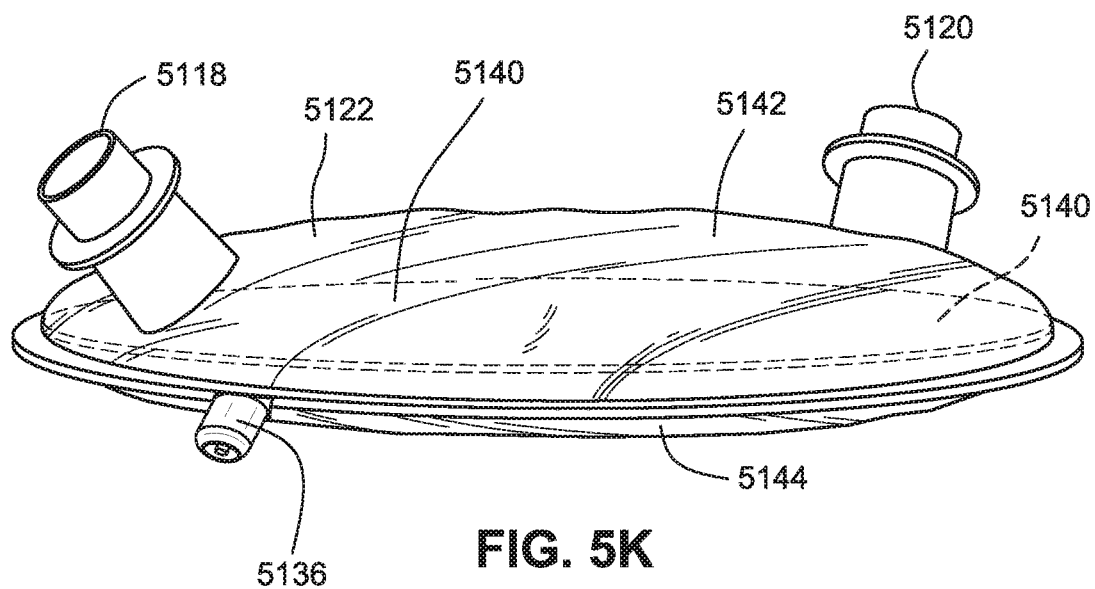

FIG. 5K shows a flexible reservoir according to one form of the present technology.

Figure 5L:
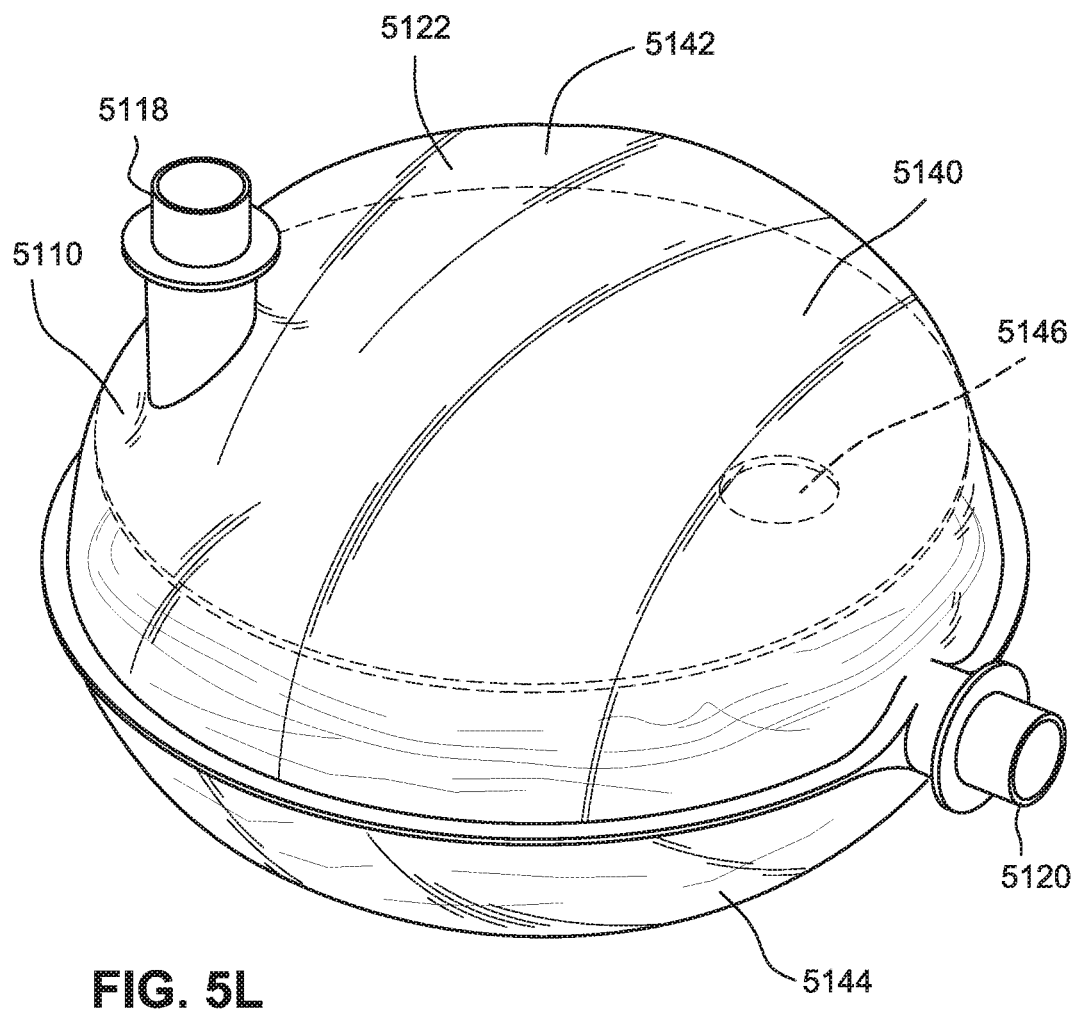

FIG. 5L shows a flexible reservoir according to one form of the present technology.

Figure 5M:
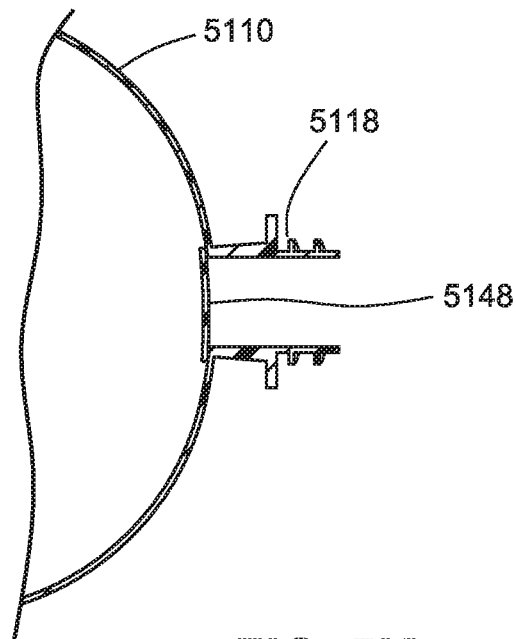

FIG. 5M shows an air inlet of a flexible reservoir according to one form of the present technology.

Figure 5N:
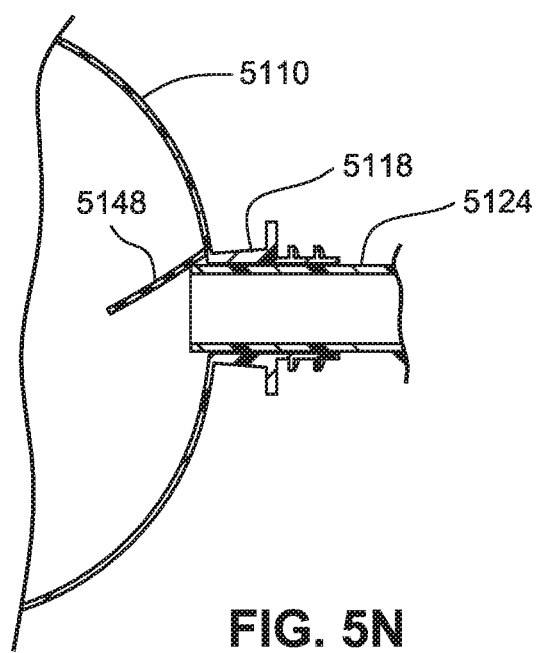

FIG. 5N shows an air inlet of a flexible reservoir according to one form of the present technology.

Figure 5O:
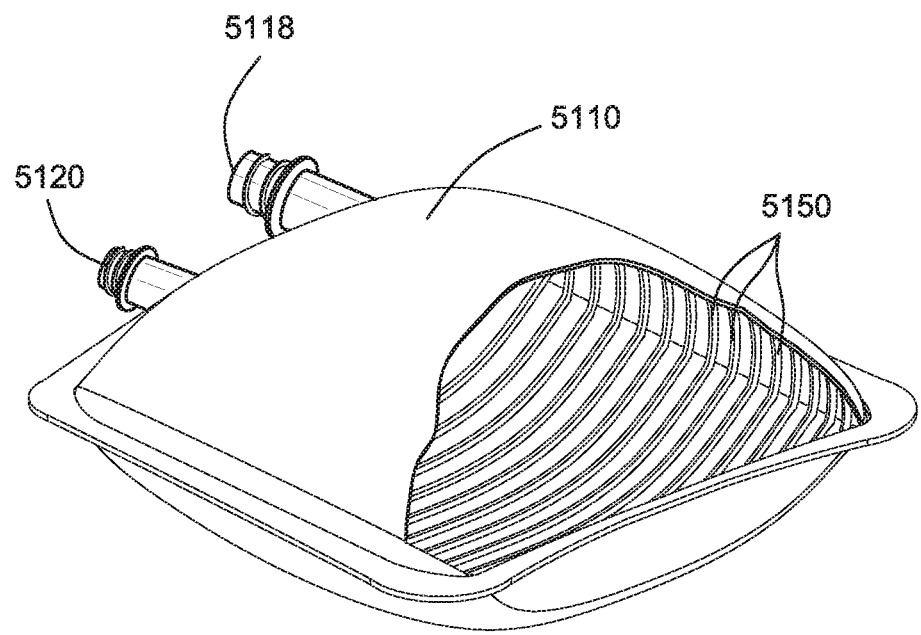

FIG. 5O shows a flexible reservoir according to one form of the present technology.

Figure 5P:
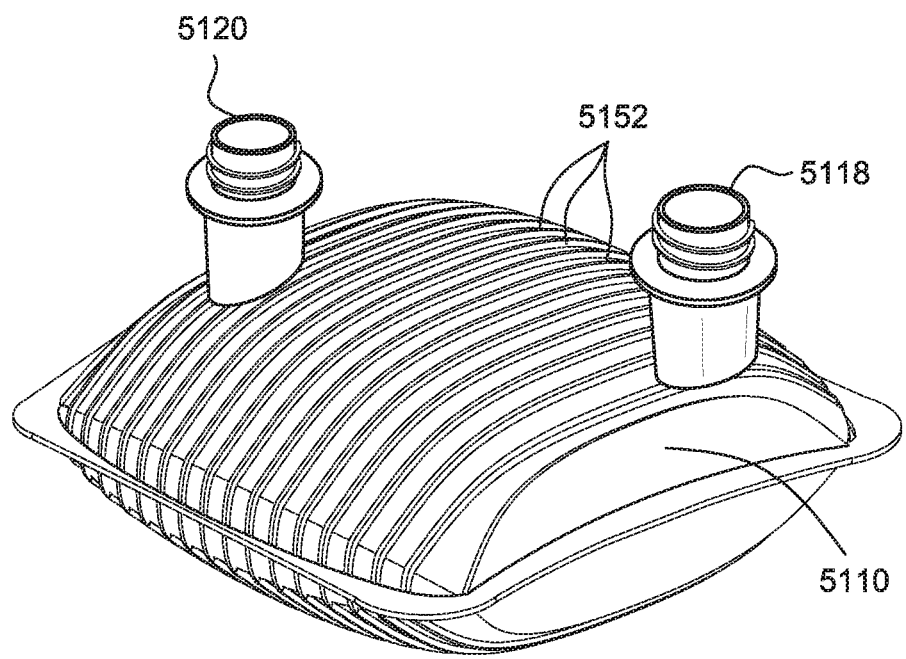

FIG. 5P shows a flexible reservoir according to one form of the present technology.

Figure 5Q:
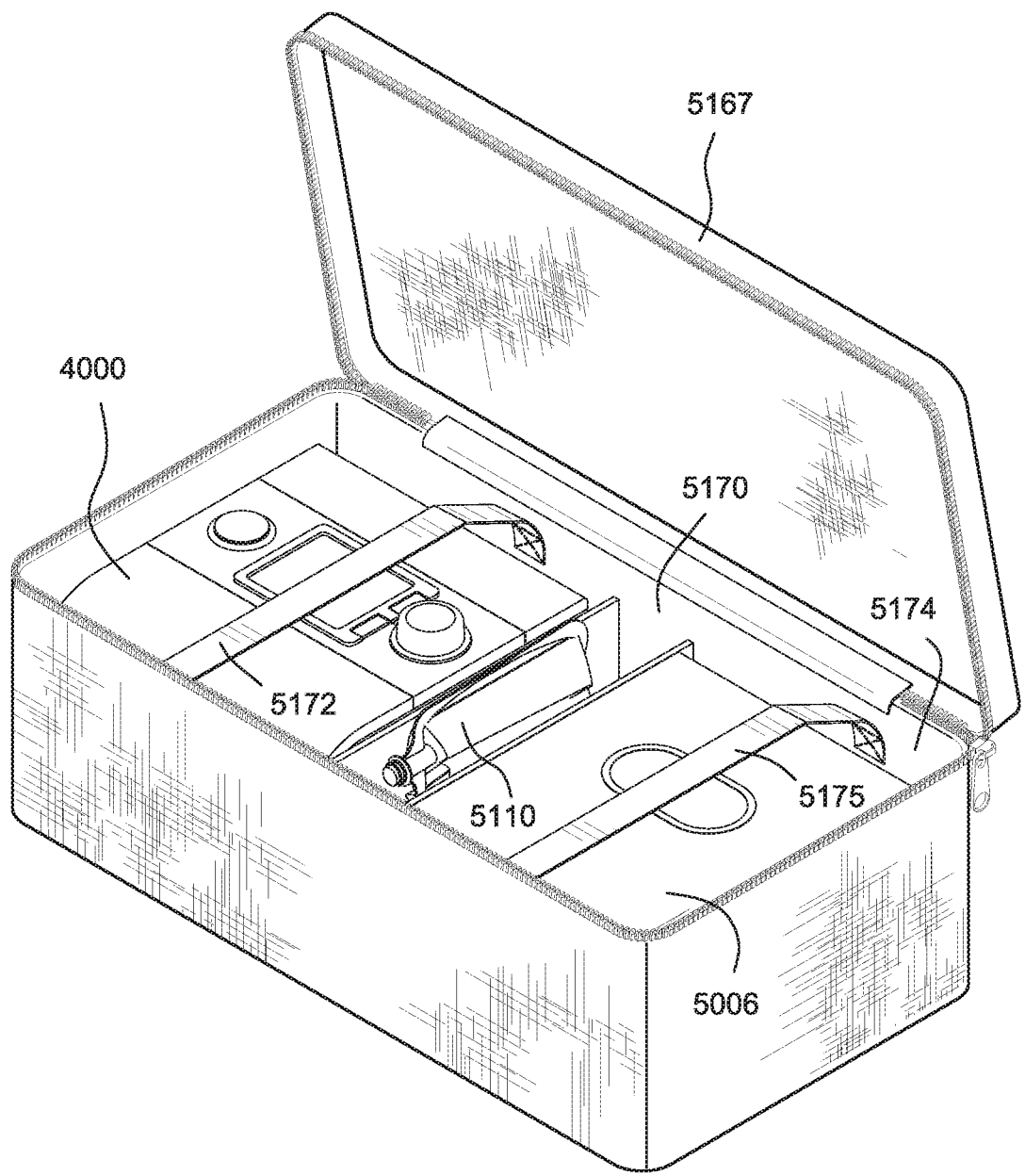

FIG. 5Q shows a travel kit according to one form of the present technology.

Figure 5R:
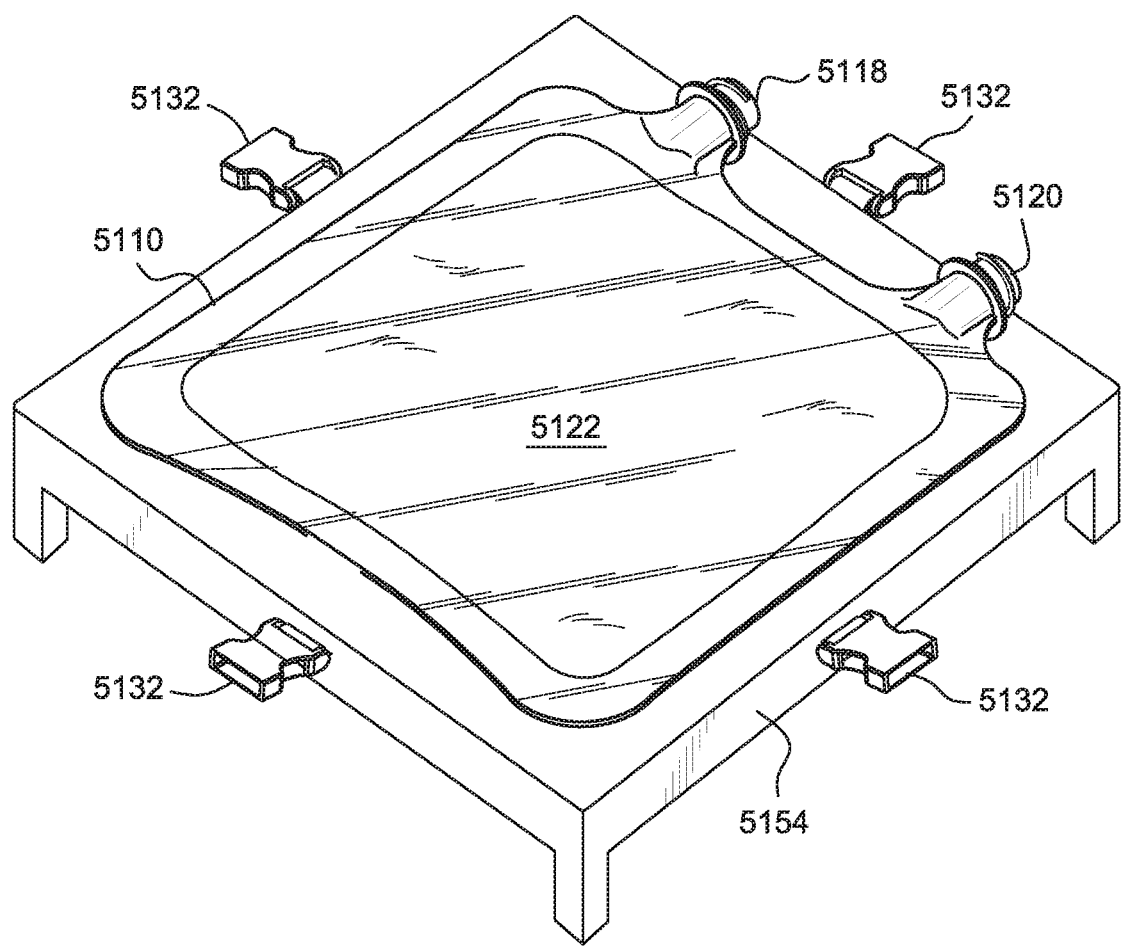

FIG. 5R shows a flexible reservoir according to one form of the present technology.

Figure 5S:
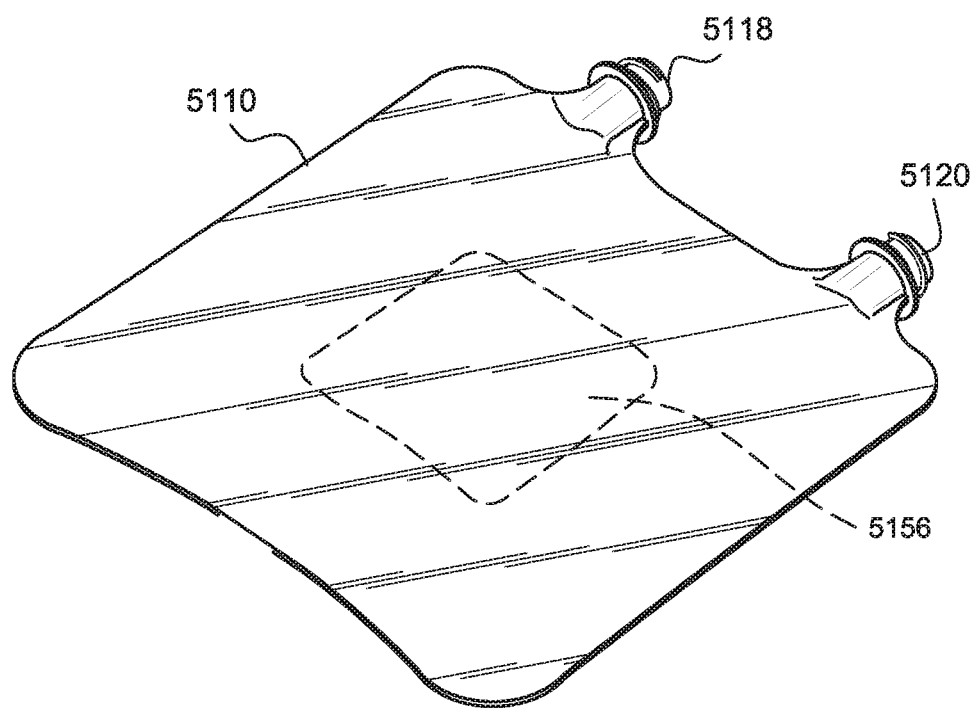

FIG. 5S shows a flexible reservoir according to one form of the present technology.

Figure 5T:
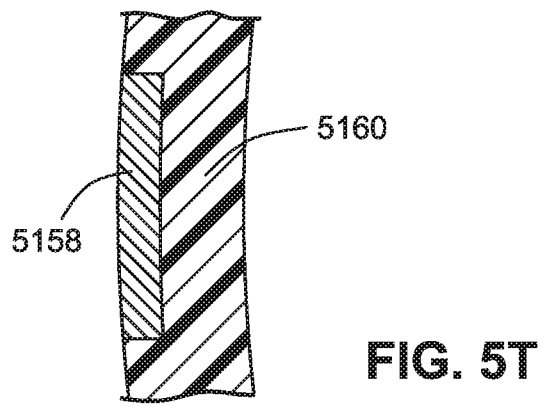

FIG. 5T shows a flexible reservoir according to one form of the present technology.

Figure 5U:
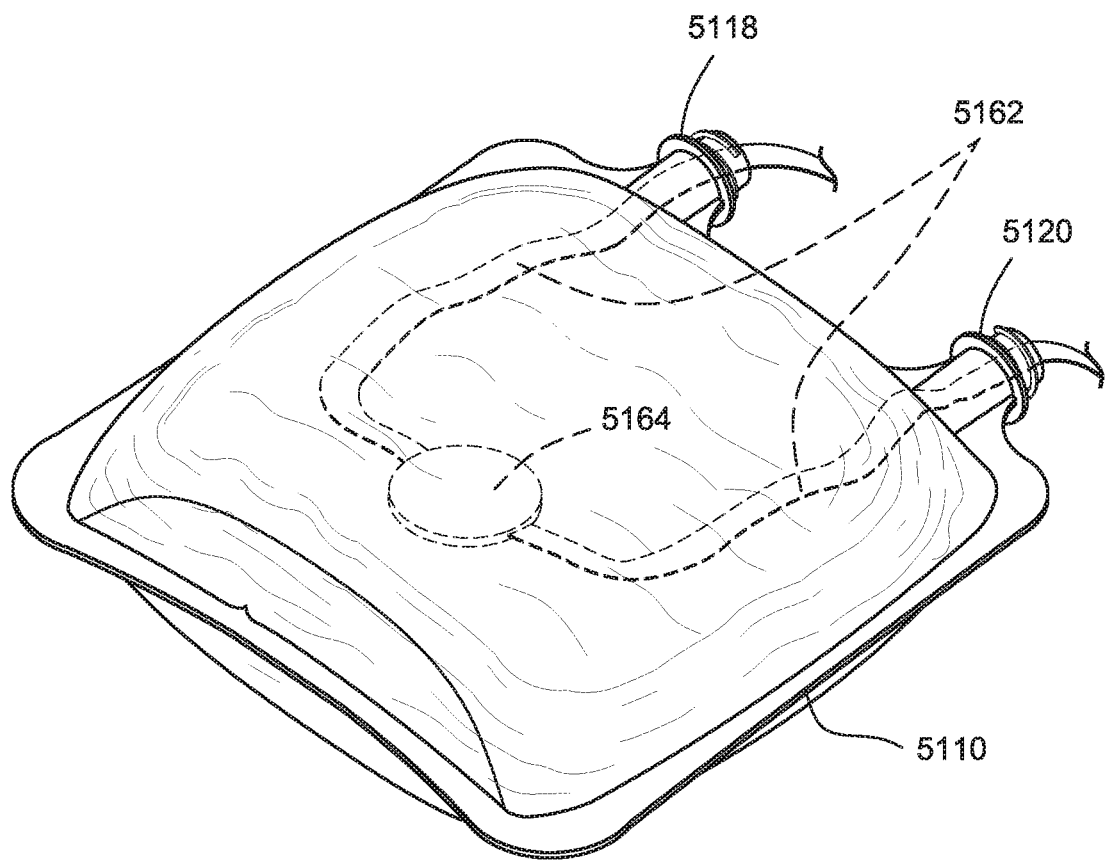

FIG. 5U shows a flexible reservoir according to one form of the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 TREATMENT SYSTEMS

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

Examples of non-invasive patient interfaces according to one aspect of the present technology include a nasal mask, a nose and mouth mask and a nasal cannula. An example of an invasive patient interface according to one aspect of the present technology includes a tracheostomy tube.

4.4 RPT DEVICE

An RPT device 4000 in accordance with one aspect of the present technology comprises mechanical and pneumatic components 4100, electrical components 4200 and is configured to execute one or more algorithms. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form the pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

Figure 1:
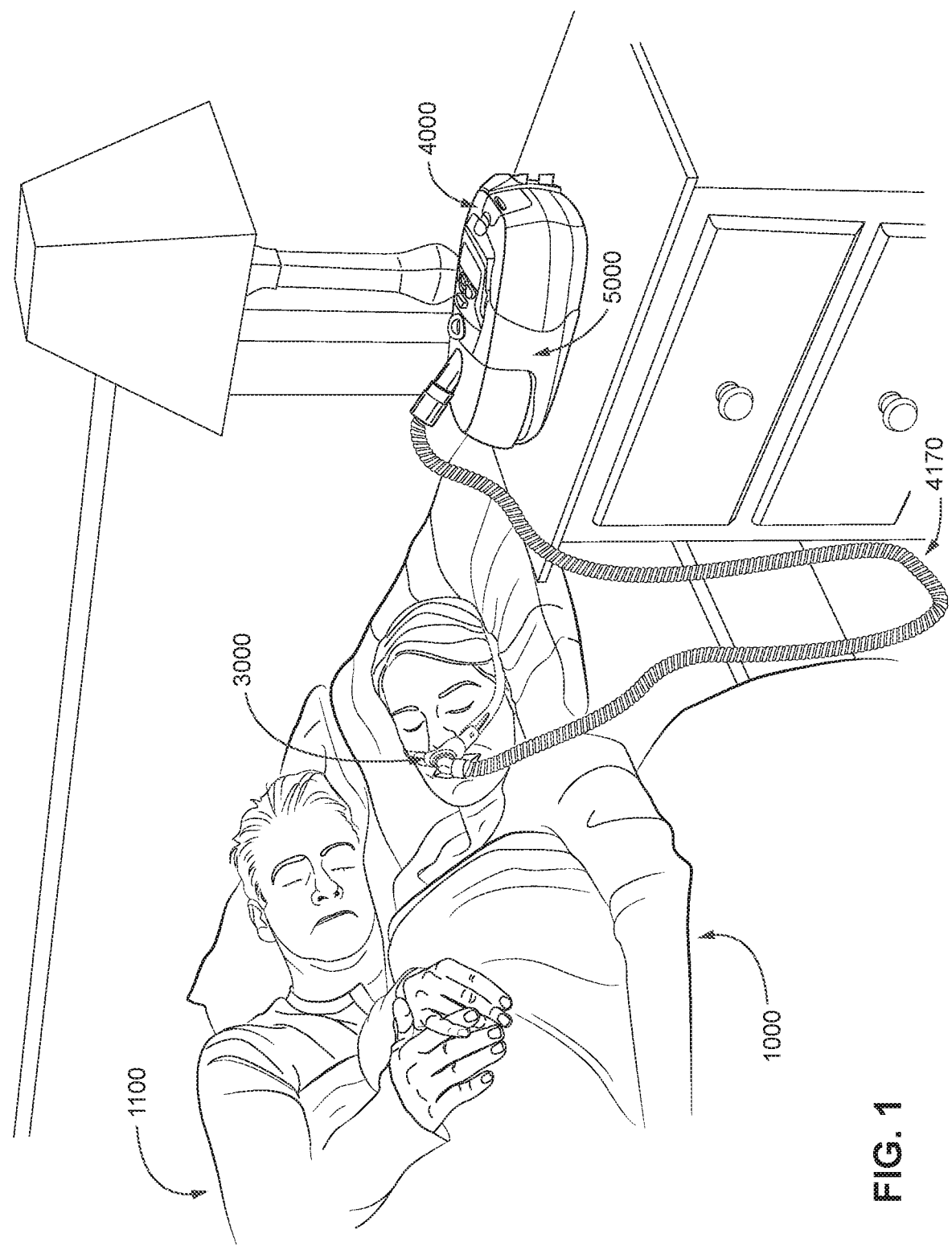
Figure 2:
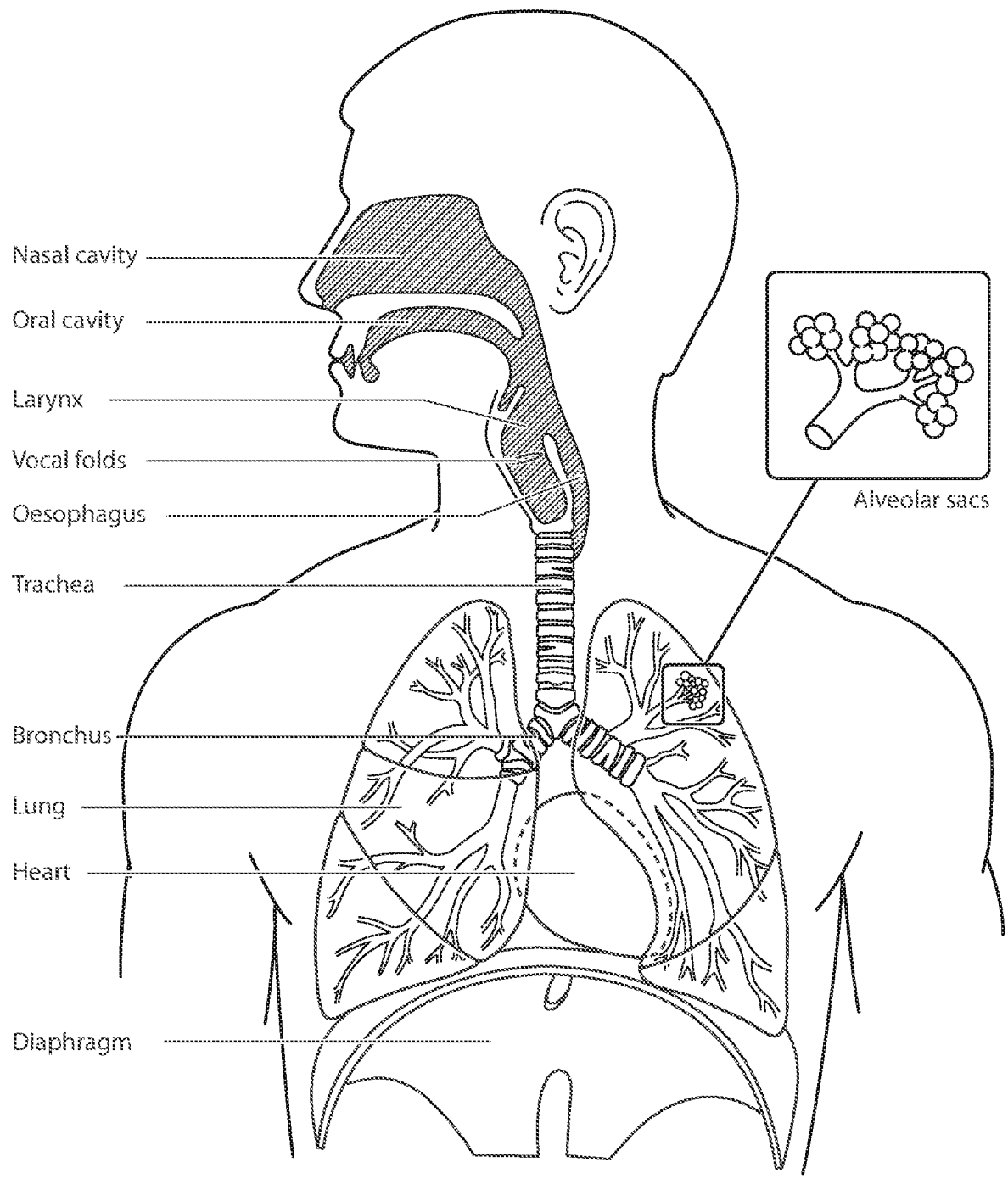
Figure 3:
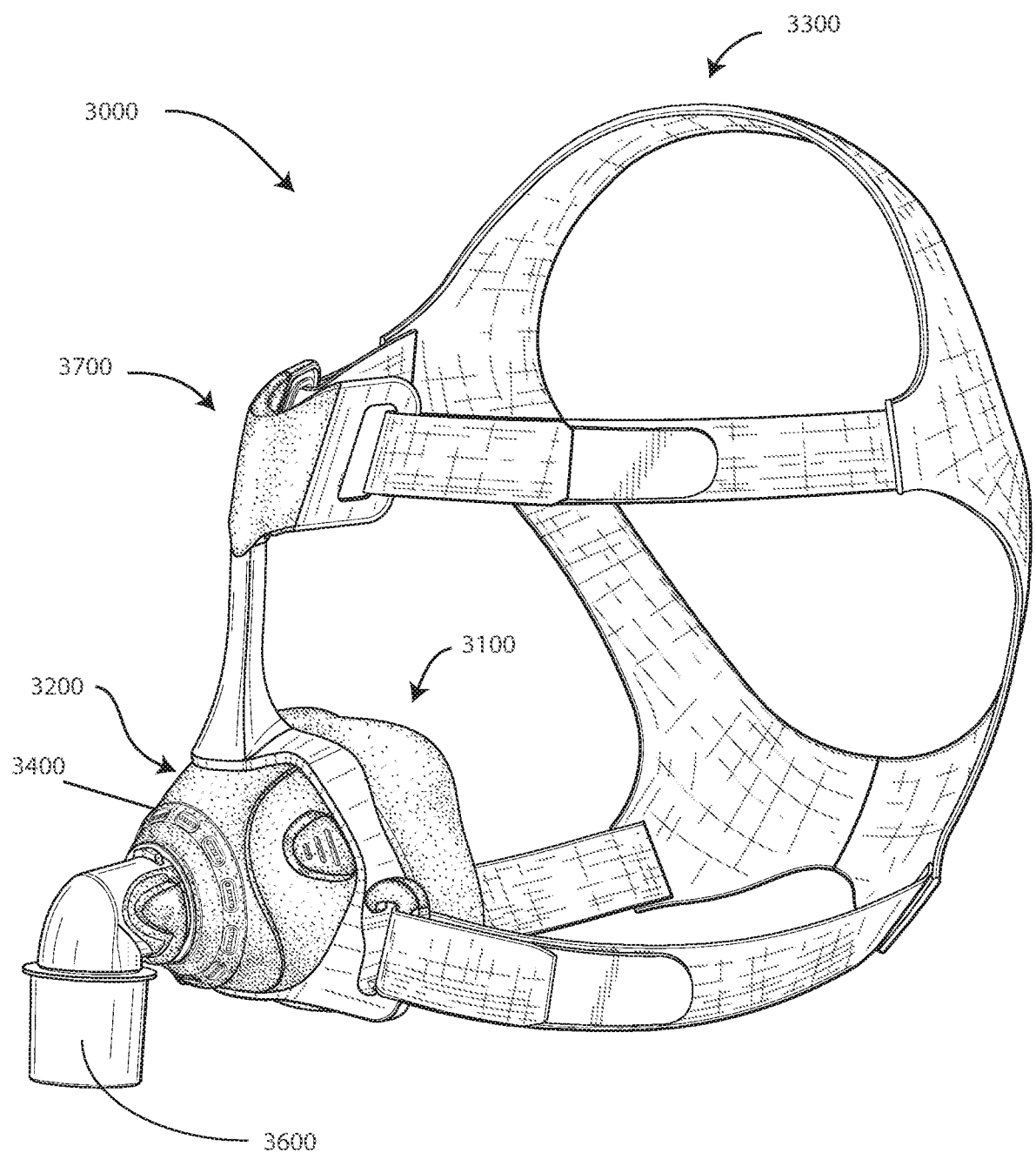
Figure 4A:
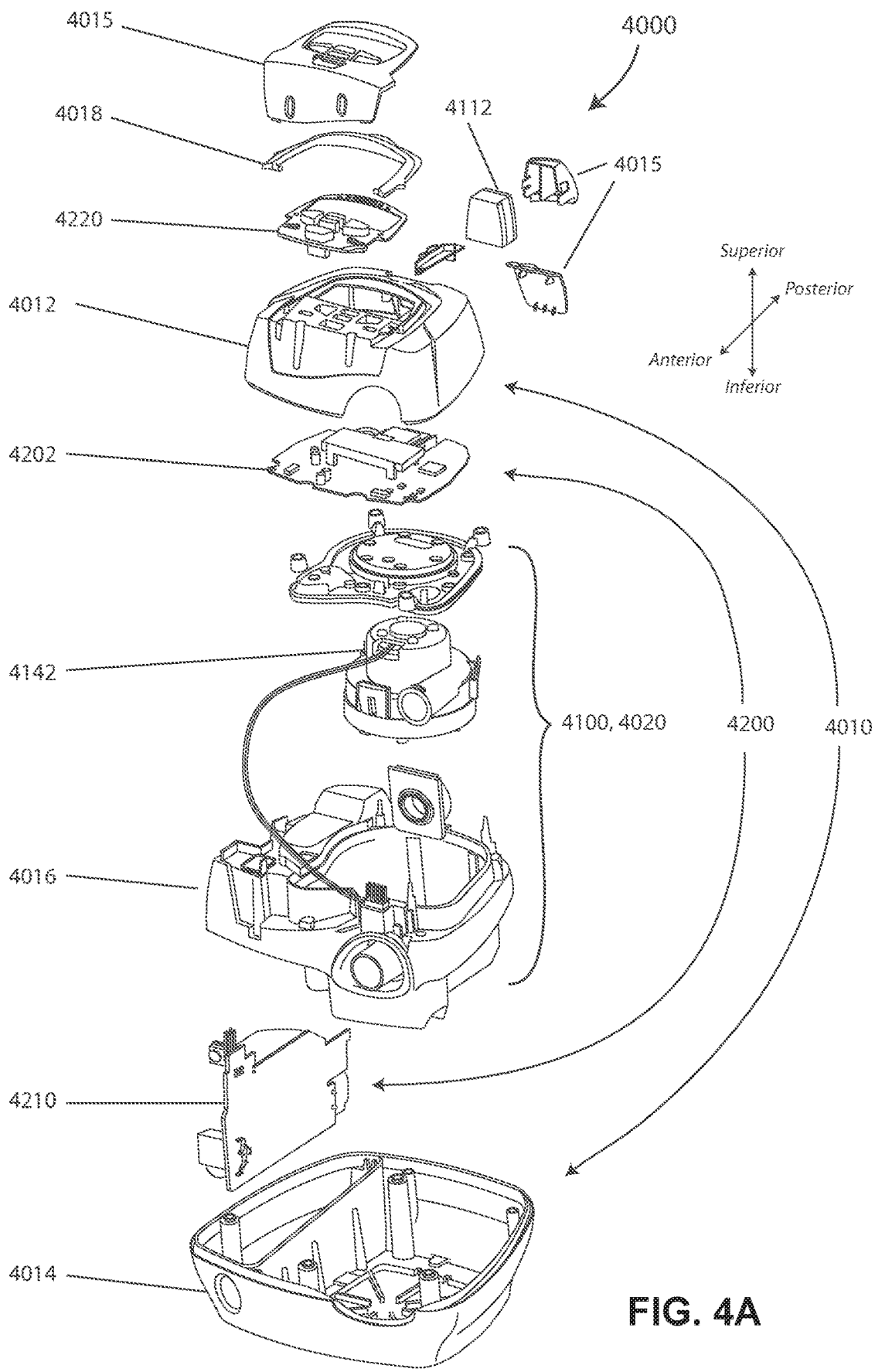
FIG. 4A shows an RPT device in accordance with one form of the present technology.
Figure 4B:
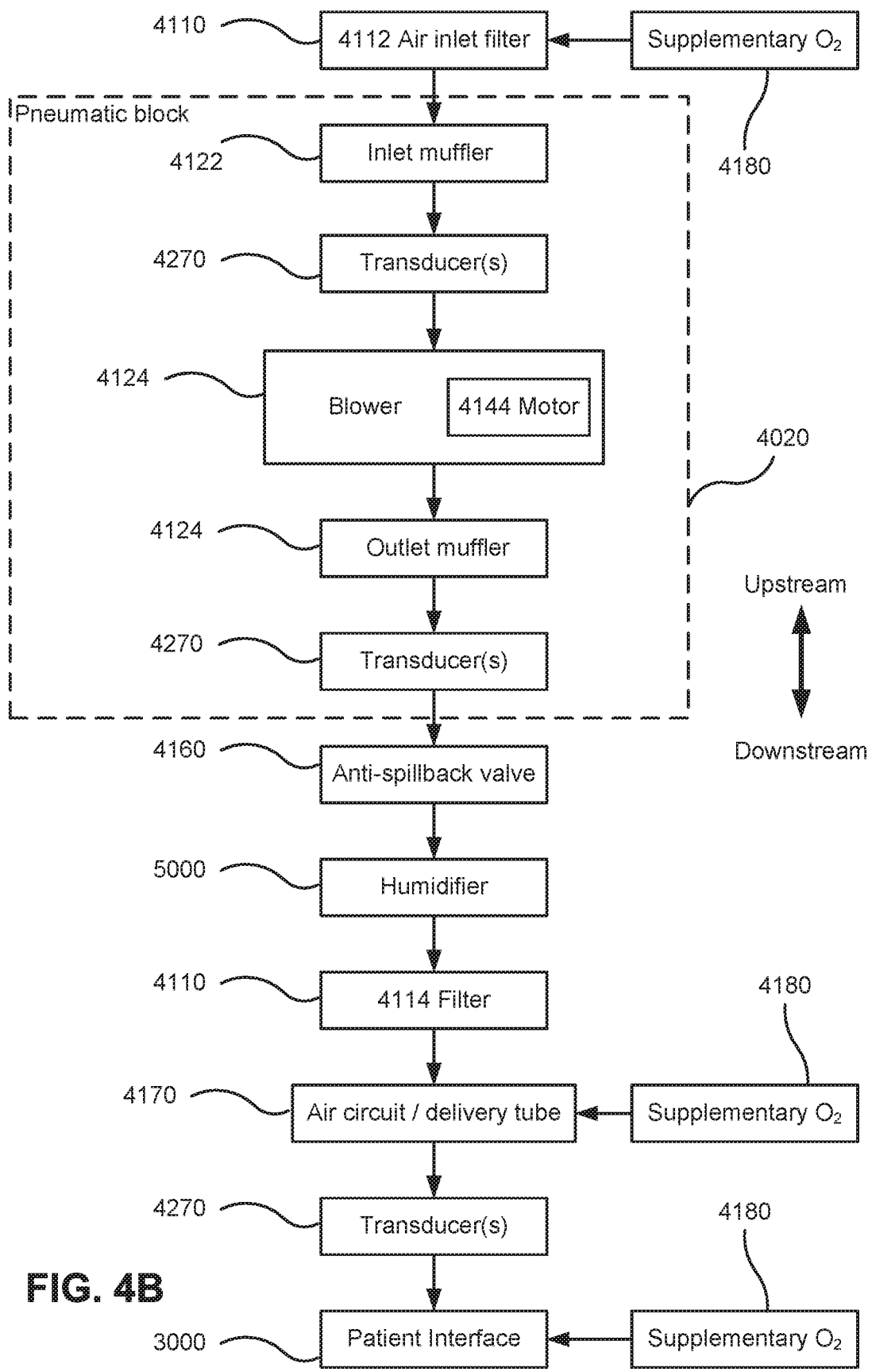
FIG. 4B is a schematic diagram of the pneumatic path of an RPT device in accordance with one form of the present technology. The directions of upstream and downstream are indicated.
Figure 4C:
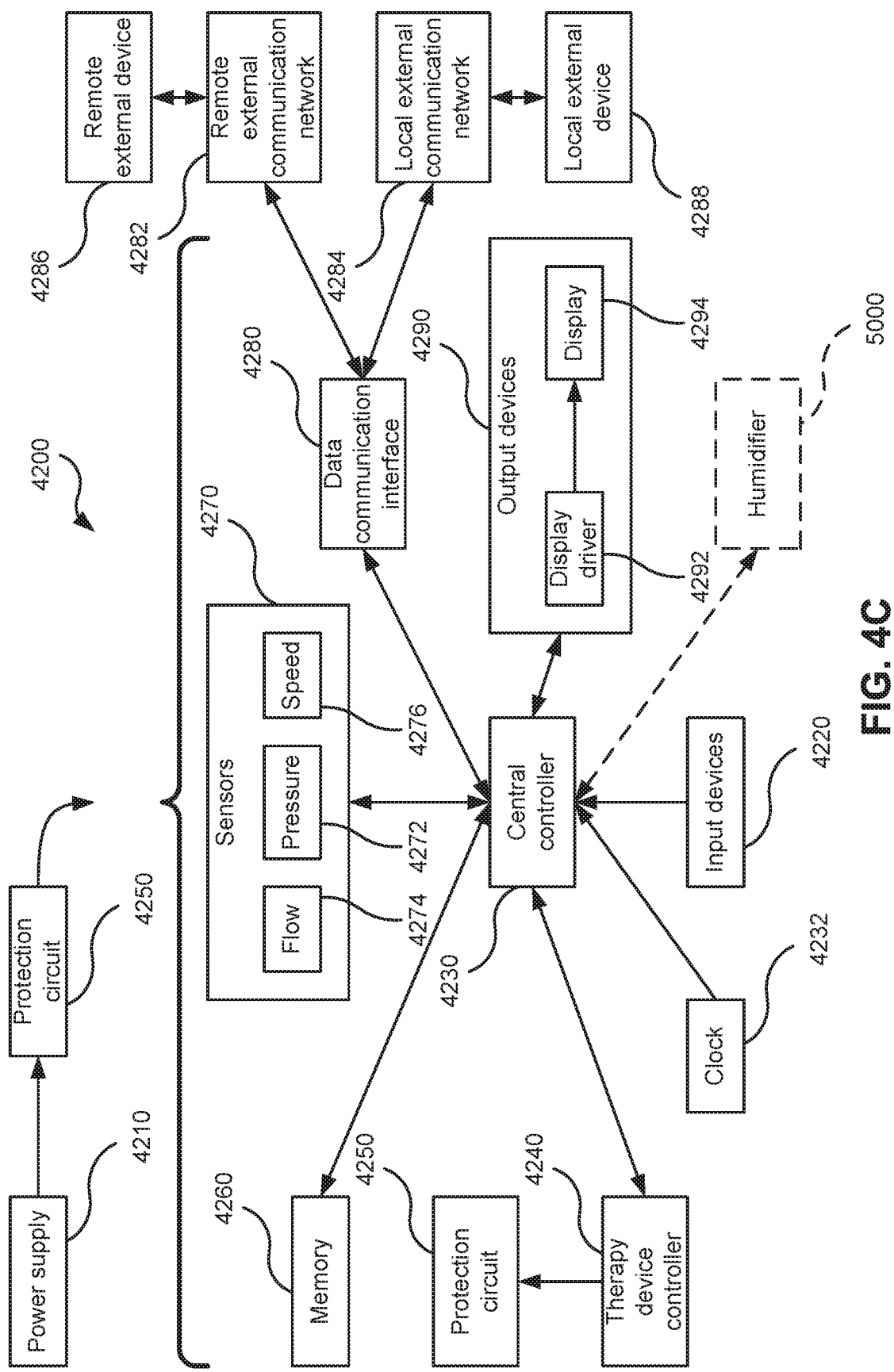
FIG. 4C is a schematic diagram of the electrical components of an RPT device in accordance with one form of the present technology.

In one form, an inlet air filter 4112 is located at the beginning of the pneumatic path upstream of a pressure generator 4140. See FIG. 4B.

In one form, an outlet air filter 4114, for example an antibacterial filter, is located between an outlet of the pneumatic block 4020 and a patient interface 3000. See FIG. 4B.

4.4.1.2 Muffler(s)

In one form of the present technology, an inlet muffler 4122 is located in the pneumatic path upstream of a pressure generator 4140. See FIG. 4B.

In one form of the present technology, an outlet muffler 4124 is located in the pneumatic path between the pressure generator 4140 and a patient interface 3000. See FIG. 4B.

4.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 liters/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

4.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate such as a total flow rate Qt from the flow rate sensor 4274 is received by the central controller 4230.

4.4.1.4.2 Pressure Sensor

A pressure sensor 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor 4272 is received by the central controller 4230.

4.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

4.4.1.5 Anti-Spill Back Valve

In one form of the present technology, an anti-spill back valve 4160 is located between the humidifier 5000 and the pneumatic block 4020. The anti-spill back valve 4160 is constructed and arranged to reduce the risk that water will flow upstream from the humidifier 5000, for example to the motor 4144.

4.4.1.6 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

4.4.2 RPT Device Electrical Components

4.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

4.4.2.3 Central Controller

In one form of the present technology, the central controller 4230 is one or a plurality of processors suitable to control an RPT device 4000.

4.4.2.4 Clock

The RPT device 4000 may include a clock 4232 that is connected to the central controller 4230.

4.4.2.5 Therapy Device Controller

In one form of the present technology, therapy device controller 4240 is a therapy control module that forms part of the algorithms executed by the central controller 4230.

4.4.2.6 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

4.4.2.7 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.7.1 Display Driver

A display driver 4292 receives as an input the characters, symbols, or images intended for display on the display 4294, and converts them to commands that cause the display 4294 to display those characters, symbols, or images.

4.4.2.7.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.5 AIR CIRCUIT

An air circuit 4170 in accordance with an aspect of the present technology is a conduit or a tube constructed and arranged in use to allow a flow of air to travel between two components such as between the pneumatic block 4020 and the patient interface 3000, between the RPT device 4000 and the humidifier 5000, or between the humidifier 5000 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used. An air circuit may be a part of an RPT device 4000 in some forms, although it may be a separate component in other forms.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in United States Patent Application No. US/2011/0023874, which is incorporated herewithin in its entirety by reference.

4.6 HUMIDIFIER

4.6.1 Humidifier Overview

In one form of the present technology there is provided a humidifier 5000 (e.g. as shown in FIGS. 5A-5C$_{[JPH1]}$) to change the temperature and/or the absolute humidity of air or gas for delivery to a patient relative to ambient air. Typically, the humidifier 5000 is used to increase the absolute humidity and increase the temperature of the flow of air (e.g. relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5C, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element (also referred to as a heater)(not shown).

In some forms, a humidifier 5000 may be separably configured with respect to the RPT device 4000. For example, the humidifier may be detachably connected to a housing of the RPT device 4000, or detachably connected via an air circuit. In other forms, a humidifier 5000 and an RPT device 4000 may be integrally constructed as a single apparatus or assembly.

4.6.2 Humidifier Mechanical Components

4.6.2.1 Humidifier Base$_{[JPH2]}$

The humidifier 5000 may comprise a humidifier base 5006 in some forms of the present technology. The humidifier base 5006 may comprise one or more components, such as: a receiving space 5112, a heating element (not shown), a flow sensor, a temperature sensor, a humidity sensor, a pressure sensor and/or a humidifier controller 5176. The humidifier base 5006 may comprise a housing enclosing one or more components. The humidifier base 5006 may be configured for example to provide a rigid structure for the humidifier 5000.

In some forms, the humidifier base 5006 may be configured to couple to, or receive, the humidifier reservoir 5110 to locate and/or secure the humidifier reservoir 5110.

The humidifier base 5006 may be located at or near a lower portion of the humidifier 5000 as shown in FIG. 5A or FIG. 5B. However, the term 'humidifier base', as used in the present document will be understood to be not limiting in terms of location with respect to the rest of the humidifier 5000. For example, the humidifier base may be located primarily on a side, top, or a bottom of the humidifier 5000 when oriented in a normal working, upright, orientation.

4.6.2.2 Humidifier Reservoir

According to one arrangement, the humidifier 5000 may comprise a reservoir 5110 configured to hold, or retain, a volume of liquid (e.g. water) to be evaporated for humidification of the flow of air. The reservoir 5110 may be configured to hold a predetermined maximum volume of water (or any other suitable liquid) in order to provide adequate humidification for at least the duration of a respiratory therapy session, such as one evening of sleep. Typically, the reservoir 5110 is configured to hold several hundred milliliters of water, e.g. 300 milliliters (ml), 325 ml, 350 ml or 400 ml. It is contemplated that in some forms, a humidifier reservoir 5110 may be larger or smaller.

According to one aspect, the reservoir 5110 is configured to add humidity to a flow of air from the RPT device 4000 as the flow of air travels therethrough. In one form, the reservoir 5110 may be configured to encourage the flow of air to travel in a tortuous path through the reservoir 5110 while in contact with the volume of water therein.

The reservoir 5110 may be constructed from a pliant, flexible material such as, for example, polyethylene, polyamide or a combination thereof. It is contemplated that the reservoir 5110 may be made of other plastics or other flexible and bio-compatible materials in combination with or in substitution of the polyethylene and polyamide. As such, the reservoir 5110 may conform to the shape of the receiving space 5112 of the humidifier 5000 for example in use.

It will be understood that the walls of the reservoir 5110 may be sized to achieve sufficiently pliant and conformal behaviour and other design requirements such as resistance to breakage and/or deformation. For example, for a first material comprising a higher elastic modulus and a higher yield strength than a second material, a smaller wall thickness may be suitable while achieving similar mechanical properties.

The humidifier 5000 may comprise one or more walls defining the receiving space 5112. The receiving space 5112 may be configured to receive the reservoir 5110, and for example may be located in the humidifier base 5006. It will be understood that a variety of shapes may be suitable for the receiving space 5112. For example, the set of walls may be orthogonally arranged as to define a prism shaped receiving space 5112 as shown in FIG. 5A, or define a non-prism shaped receiving space 5112 as shown in FIG. 5B. It is further contemplated that the set of walls may be curved to define a hemispherical receiving space 5112 (not shown). In addition, the pliant nature of the reservoir 5110 may allow for the reservoir 5110 be used with more than one type of humidifier 5000 or RPT device 4000, such as to suit a plurality of shapes of the receiving space 5112. Such a design may be beneficial for a manufacturer, distributor and consumer alike for example, as it may reduce manufacturing burden, inventory, costs and likelihood of wastage.

It should be understood that in configurations where the reservoir 5110 is received directly by the RPT device 4000, the receiving space 5112 may be defined by one or more walls of the RPT device 4000.

The reservoir 5110 may also be structured to exist in a plurality of configurations. For example, the reservoir 5110 may be convertible between a storage (or transport) configuration and a working configuration. The reservoir 5110 in the storage configuration may be collapsed, folded and/or rolled for example to reduce its volume. In some forms, the reservoir 5110 may be collapsible to a flat plate for improved stacking with other collapsed reservoirs.

In some forms, a plurality of reservoirs 5110 may be stored together with (for example inside) the humidifier 5000, such that a kit may be provided for convenient storage, sale and transport. For example, a plurality of reservoirs 5110 in their storage configurations may be stored in the humidifier 5000, such as in the receiving space 5112 to reduce the volume for transport or another storage compartment for each access by the patient.

In the working configuration, the reservoir 5110 may comprise an increased volume, such as expanded by the patient, receipt of a volume of water and/or a flow of air. Thus, the reservoir 5110 may expand to conform to a shape of the receiving space 5112, such as during use or when filled with water.

In addition, as shown in FIG. 5C, a humidifier 5000 may not comprise a humidifier base. In some forms of the present technology, the reservoir 5110 may be directly coupled to the RPT device 4000 by way of a connector (e.g. an ISO connector) connecting the outlet of the RPT device 4000 to the inlet of the reservoir 5110. It is also contemplated that additional coupling mechanisms such as adhesive, tabs, grooves, clips, notches, frames, etc., may be used to couple the reservoir 5110 directly to the RPT device 4000. Of course, the reservoir 5110 may be fluidly connected to the RPT device via an air circuit 4170.

4.6.2.2.1 Humidifier Reservoir Shape

FIGS. 5A-5U illustrate reservoirs 5110 having rectangular and circular shapes in one or more cross-sections. However, the shape of the reservoir 5110 need not be limited to those illustrated in FIGS. 5A-5T or those explicitly described herewithin. For example, the reservoir 5110 may comprise one or more of triangular, cylindrical, pyramidal, prismatic or any polygonal shapes, in cross-section, elevation and/or plan views for example. It should be noted that the shape of the reservoir 5110 may be dictated by the shape of the receiving space 5112. In particular, the shape of the reservoir 5110 may be chosen to maximize the surface area of the reservoir 5110 in direct contact with the walls of the receiving space 5112 when the reservoir 5110 is received by the receiving space 5112 and in use.

4.6.2.2.2 Humidifier Reservoir Engaging Portion

As shown in FIGS. 5D and 5E, the reservoir 5110 may include an engaging portion 5114. The engaging portion 5114 can facilitate positioning and/or fastening of the reservoir 5110 with respect to the humidifier 5000. For example, engaging portion 5114 may position the reservoir 5110 within the receiving space 5112 and/or fasten the reservoir 5110 to a complementarily shaped portion of the receiving space 5112. The engaging portion 5114 may be, for example, one or more tabs, grooves, clips, notches, frames or any other mechanism capable of removably positioning and/or securing the reservoir 5110 to the humidifier base 5006. The fastening (or securing) may be releasable in some forms of the present technology such that the water reservoir 5110 may be replaced.

In one example, the engaging portion 5114 may be a tab configured to be inserted (e.g. by sliding) into a complementary slot in the humidifier base 5006 (not shown). The tab may be then releasably clamped in the slot to locate and secure the reservoir 5110 with respect to the humidifier 5000.

It is contemplated that adhesive may be provided on one or more surfaces of the reservoir 5110 (in addition to or instead of the engaging portion 5114) to secure the reservoir 5110 to the humidifier base 5006. In addition, the reservoir 5110 may include sensors (or transducers) 5116 to interact with sensors on the humidifier base 5006 for determining the presence of the reservoir 5110. It should be understood that the engaging portion 5114 may be configured to directly couple with the RPT device 4000 in accordance with the configuration shown in FIG. 5C.

4.6.2.2.3 Humidifier Reservoir Inlet and Outlet

As illustrated in FIGS. 5D and 5E, the reservoir 5110 may have an air inlet 5118 and an air outlet 5120. The air inlet 5118 and the air outlet 5120 may be oriented in the same direction as illustrated in FIG. 5D. Alternatively, the air inlet 5118 and the air outlet 5120 may be oriented in different directions as illustrated in FIG. 5E. In addition, the air inlet 5118 and air outlet 5120 may be projections from a main body 5122 (e.g. as shown in FIG. 5E). Alternatively, one or both of the air inlet 5118 and the air outlet 5120 may simply be apertures in the main body 5122.

One or both of the air inlet 5118 and the air outlet 5120 may be collapsible. For example, both of the air inlet 5118 and the air outlet 5120 may be collapsible such that the entire reservoir 5110 may be collapsed into the storage configuration. In some forms, the reservoir 5110 may be partly collapsible such that one or both of the air inlet 5118 and the air outlet 5120 may not be collapsed in the storage configuration. For example, the air inlet 5118 and the air outlet 5120 may be configured as rigid tubular structures.

The air inlet 5118 illustrated in FIGS. 5D and 5E may be configured to be inserted into a connector 5124 of the humidifier base 5006 (as shown in FIG. 5B) or an outlet of the RPT device 4000. Alternatively, the air inlet 5118 may be configured to receive the connector 5124 of the humidifier base 5006 or the outlet of the RPT device 4000. It is also contemplated that the air inlet 5118 may not be inserted into or receive the connector 5124 of the humidifier base 5006 or the outlet of the RPT device 4000. Instead, the air inlet 5118 may be configured to engage the humidifier base 5006 or the RPT device 4000 as a face seal. The face seal may be pressure activated, for example be configured to establish a seal, or to increase a sealing force upon an increase in interior pressure, such as when therapy is initiated. The face seal may comprise a bellows portion, for example any one of those described in U.S. Pat. No. 8,544,465, the contents of which are incorporated herewithin by reference.

In one form, the air inlet 5118 may comprise a face configured to engage a compliant portion (e.g. a bellows portion) located on humidifier base 5006 or the RPT device 4000. In this configuration, the compliant portion would abut the face on the reservoir 5110 surrounding the air inlet 5118 to form a face seal, thereby sealing the air path. It is further contemplated that the air inlet 5118 may comprise a compliant portion (e.g. a bellows portion) configured to abut against a complementary face located on the humidifier base 5006 and/or the RPT device 4000 to form a face seal.

Similar to the air inlet 5118, the air outlet 5120 illustrated in FIGS. 5D and 5E may be configured to be inserted into a connector 5126 of the humidifier base 5006 (as shown in FIG. 5A) or an air delivery tube (not shown). Alternatively, the air outlet 5120 may be configured to receive the connector 5126 of the humidifier base 5006 or the air delivery tube.

In some forms, the air inlet 5118 and/or the air outlet 5120 may comprise an ISO standard connector, such as for connecting to a humidifier base 5006, the RPT device 4000 or an air circuit 4170. The ISO standard connector may be as specified in *ISO* 5356-1:2015 *Anaesthetic and respiratory equipment—Conical connectors—Part 1—Cones and sockets*, for example comprising a 15 mm diameter or a 22 mm diameter.

It is also contemplated that the air outlet 5120 may not be inserted into or receive the connector 5126 of the humidifier base 5006. Instead, the air outlet 5120 may comprise a compliant portion (e.g. a bellows portion) configured to engage the humidifier base 5006 to form a face seal. In this configuration, the compliant portion (e.g. a bellows portion) would abut a portion of the reservoir 5110 surrounding the air outlet 5120 to form a sealed air path. It is further contemplated that the air outlet 5120 may comprise a compliant portion (e.g. a bellows portion) configured to abut against a face of the humidifier base 5006 to form a face seal.

FIGS. 5A-5F show the reservoir 5110 with one air inlet 5118 and one air outlet 5120. In those configurations, liquid may be poured into the reservoir 5110 through either of the air inlet 5118 and the air outlet 5120. However, as shown in FIG. 5G, the reservoir 5110 may include a port 5136 in addition to the air inlet 5118 and the air outlet 5120. The port 5136 may function as an inlet/outlet for liquid. In another configuration (shown in FIG. 5H), the reservoir 5110 may include only one opening 5138 to act as the air inlet, the air outlet and for supplying the reservoir 5110 with water.

4.6.2.2.4 Humidifier Reservoir Assembly

As illustrated in FIGS. 5D and 5E, the reservoir 5110 may comprise a single unitary main body 5122 configured to substantially enclose the interior volume of the reservoir 5110. Alternatively, as shown in FIG. 5F, the main body 5122 of the reservoir 5110 may be disassembled to a plurality of components.

In one form, the main body 5122 may comprise a top portion 5128 and a bottom portion 5130 removably secured to each other by way of any number of securing mechanisms 5132 including but not limited to snap fit connections, zip-lock sealing zipper, etc. The main body 5122 may further comprise a seal 5134 sandwiched between the top portion 5128 and the bottom portion 5130. Of course, it will be understood that the main body 5122 may be configured in any number of ways that allows disassembly into a plurality of components.

The reservoir 5110 may be disassembled, for example, into rigid components and flexible components. Additionally, or alternatively, the reservoir 5110 may be disassembled into reusable and disposable components. In some forms the reservoir 5110 may be disassembled such the plurality of disassembled components may be more readily packaged, such as for storage (or transport). In one form, the reservoir 5110 may disassemble into a plurality of components, wherein a first component may be complementary to, nested in, or engage with, a second component, to a storage configuration (e.g. collapsed, flattened, rolled or folded) different to the in-use configuration of the reservoir 5110.

4.6.2.2.5 Humidifier Reservoir Inflation and Deflation

As shown in FIGS. 5I and 5K, the reservoir 5110 may initially be in a deflated condition, such as during storage and/or transport. The reservoir 5110 may inflate or expand (FIGS. 5J and 5L) upon supplying the reservoir 5110 with water and/or pressurized gas. The pressurized gas may be supplied during a therapy session.

In addition, the expansion of the reservoir 5110 (due to the addition of liquid and/or the addition of pressurized gas) may form and/or reinforce the seal between the air inlet 5118 and the connector 5124 of the humidifier base 5006 as well as the seal between the air outlet 5120 and the connector 5126 of the humidifier base 5006. For example, the expansion of the reservoir 5110 may bias the air inlet 5118 against the connector 5124 of the humidifier base 5006 and may bias the air outlet 5120 against the connector 5126 of the humidifier base 5006. It is contemplated that the force exerted by the expansion of the reservoir 5110 may also prevent the connection between the air inlet 5118 and the connector 5124 of the humidifier base 5006 from being broken and may prevent the connection between the air outlet 5120 and the connector 5126 of the humidifier base 5006 from being broken.

The expansion of the reservoir 5110 may also bias the main body 5122 against an interior surface of the receiving space 5112. The expansion of the reservoir 5110 may locate the main body 5122 in a working position within the receiving space 5112, and/or engage the main body 5122 with respect to the receiving space 5112 such that the reservoir 5110 may be frictionally secured to the humidifier base 5006 due to the force exerted by the expansion of the reservoir 5110.

4.6.2.2.6 Humidifier Reservoir Backflow Prevention

It is contemplated that the reservoir 5110 may also include a backflow (spillback) prevention system for preventing the flow of liquid through the air inlet 5118. For example, as illustrated in FIGS. 5J and 5K, the reservoir 5110 may include a divider 5140 to prevent liquid flowing through the air inlet 5118. The divider 5140 may divide the reservoir 5110 into two chambers (i.e., a first chamber 5142 and a second chamber 5144). In addition, as shown in FIG. 5L, an opening 5146 in the divider 5140 may allow pressurized gas to communicate with both the first and second chambers 5142, 5144. The opening 5146 may be located as far away from the air inlet 5118 as possible, such as at or near a geometric centre of the main body 5122. Such a configuration may have the effect of allowing the reservoir to rotate from an "in use" position and still prevent liquid from flowing through the air inlet 5118. It should be noted that in this configuration, the air outlet 5120 may be the outlet of the second chamber 5144.

As shown in FIG. 5K, the divider 5140 may not have an opening. Instead, the divider 5140 may be comprised of a gas permeable membrane that allows pressurized gas and water vapor to flow through the divider 5140 but prevents liquid from flowing through the divider 5140. In this configuration, the reservoir 5110 may be prefilled with liquid or liquid may be supplied and drained by way of the port 5136 formed adjacent the second chamber 5144.

In addition, the divider 5140 may have the same flexibility as the rest of the reservoir 5110. For example, the divider 5140 may be formed from the same material as the exterior walls of the reservoir 5110. Alternatively, the divider 5140 may be more rigid than the rest of the reservoir 5110. In the "more rigid" configuration, the divider 5140 may provide structural support to the reservoir 5110 so that the reservoir 5110 may be both conformable to the humidifier base 5006 and be able to maintain some basic shape when removed from the humidifier base 5006.

As illustrated in FIGS. 5M and 5N, the air inlet 5118 may include a check valve 5148 biased in the closed position. The check valve 5148 may be configured so that a predetermined pressure overcomes the biasing force maintaining the check valve 5148 in the closed position. The predetermined pressure may have the effect of opening the check valve 5148 and preventing the liquid in the reservoir 5110 from flowing through the air inlet 5118.

It is contemplated that the check valve 5148 may also be configured to seal the air inlet 5118 when the reservoir 5110 is separated from the humidifier base 5006. In this configuration, insertion of the connector 5124 of the humidifier base 5006 may push the check valve 5148 open when the connector 5124 of the humidifier base 5006 is inserted into the air inlet 5118.

It is further contemplated that the air inlet 5118 may have multiple check valves 5148 and that the multiple check valves 5148 may be positioned in series with each other. The outermost check valve 5148 may be configured to open when the connector 5124 of the humidifier base 5006 is inserted into the air inlet 5118 and the additional one or more check valves 5148 in the air inlet 5118 may be configured to open when the predetermined air pressure is provided to the air inlet 5118.

It should be noted that although only the check valve and divider configurations have been disclosed above with respect to backflow prevention, the backflow prevention system is not limited to the configurations discussed above.

4.6.2.2.7 Humidifier Reservoir Rigidizing Structures

As can be seen in FIGS. 5O and 5P, the reservoir 5110 may include internal and/or external rigidizing structures to provide additional of rigidity to the reservoir 5110, for example to the main body 5122. The rigidizing structure may be in the form of one or more ribs 5150 extending across an internal surface of the reservoir 5110. The one or more ribs 5150 may extend completely across the reservoir 5110 or may only extend across a portion of the reservoir 5110. In addition, the ribs 5150 may form any type of pattern that would result in a particular characteristic of rigidity. For example, the ribs 5150 may be positioned to provide rigidity one direction while allowing for complete conformability in a second direction.

As discussed above, the reservoir 5110 may include an external structure to provide some level of rigidity to the reservoir 5110. For example, the external structure may be an exoskeleton 5152. Similar to the one or more ribs 5150, the exoskeleton 5152 may be provided in any number of patterns designed to provide a particular characteristic of rigidity. For example, the exoskeleton 5152 may be configured to provide a significantly higher rigidity in one direction than in a second, orthogonal, direction, thus allowing conformability in the second direction.

4.6.2.2.8 Humidifier Reservoir Kit

It is contemplated that the reservoir 5110 may be packaged as a kit to be used with one or more types of humidifier base 5006. The packaged reservoir 5110 may be provided with or without water. In addition, each packaged kit may include one or more prefilled or non-prefilled reservoirs 5110. The kits could be provided in their collapsed form in order to be stackable and allow for bulk transport.

For example, the reservoir 5110 may be configured to be folded or otherwise manipulated to a travel configuration. The reservoir 5110 may be folded, rolled, wrapped, flattened or otherwise reduced in size (e.g., in volume and/or cross-section areas), for example to be fitted into the RPT device 4000, or a travel bag.

An exemplary travel kit is illustrated in FIG. 5Q and may comprise a travel bag 5167 including a first receptacle 5168 configured to receive the RPT device 4000, and a second receptacle 5170 configured to receive the reservoir 5110 in its travel configuration, wherein a volume of the reservoir 5110 (and the volume of the second receptacle 5170) may be smaller than the volume of the reservoir 5110 in its working, expanded configuration. A securement strap 5172 may retain the RPT device 4000 in the first receptacle 5168.

In one example, the first receptacle 5168 may comprise a cavity shaped as a prism to receive an RPT device 4000 and the second receptacle 5170 may comprise a slot-shaped cavity configured to receive the reservoir 5110 in its travel configuration.

In some forms, the travel bag 5167 may be additionally configured to receive the humidifier base 5006 in a third receptacle 5174. A securement strap 5175 may retain the humidifier base 5006 in the third receptacle 5174. In either configuration, the humidifier base 5006 and/or the RPT device 4000 may be configured to store the reservoir 5110 in its travel configuration in lieu of the second receptacle 5170 described above.

In addition, reservoirs 5110 provided in kits may include frames 5154 (as illustrated in FIG. 5R) with engagable portions configured to secure the reservoir 5110 to the humidifier base 5006 prior to expansion of the reservoir 5110. In addition, kits may be matched with particular CPAP units or be configured to be used with multiple types of CPAP units. Also, the kits may include different versions of the reservoir 5110 with different levels of durability. More durable reservoirs 5110 would be suitable for travel.

In addition, or as an alternative, prior to first use, the air inlet 5118 and/or the air outlet 5120 may be sealed by, for example, frangible seals and/or perforations that could be opened for use. It is contemplated that the seal could be punctured by the insertion of the connector 5124 of the humidifier base 5006 into the air inlet 5118. In addition, the air outlet seal could be punctured by inserting the connector 5126 of the humidifier base 5006 into the air outlet 5120 or securing an air delivery tube to the air outlet 5120.

It is contemplated that the reservoir 5110 may be a single-use reservoir or a multi-use reservoir.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.6.2.3 Conductive Portion

According to one arrangement as illustrated in FIG. 5S, the reservoir 5110 may comprise a conductive portion 5156 configured to allow efficient transfer of heat from a heating element (not shown) of the humidifier base 5006 to the volume of liquid in the reservoir 5110. In one form, the conductive portion 5156 may be arranged as a plate, although other shapes may also be suitable. In addition, the conductive portion 5156 may be located on a bottom surface of the main body 5122 of the reservoir 5110. All or a part of the conductive portion 5156 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

In addition, the conductive portion 5156 may be more rigid than the rest of the reservoir 5110. As such, the conductive portion 5156 may act similarly to the one or more ribs 5150 and/or the exoskeleton 5152 disclosed above. In other words, the conductive portion 5156 may provide a particular rigidity characteristic, e.g., providing rigidity one direction while allowing for complete conformability in a second direction. In addition, it is contemplated that the conductive portion 5156 may provide no additional rigidity to the reservoir 5110. In particular, the conductive portion 5156 would have the same flexibility as the rest of the main body 5122 of the reservoir 5110. Such an arrangement would not include a metal conductive plate.

It is also contemplated that the entire reservoir 5110 may be made of thermally conductive material (or material with low thermal impedance) such as, for example, polyethylene or some other thermally conductive plastic. In this arrangement, the base unit heating element (not shown) may be positioned to thermally engage multiple walls of the reservoir 5110 such that heat from the base unit heating element (not shown) may be conveyed through more than one surface of the reservoir 5110.

The thickness of exterior walls of the reservoir 5110 may be sized to facilitate the transfer of heat from the humidifier base heater (not shown) to liquid inside the reservoir 5110. For example, the walls may be within a range of about 0.1 mm to about 1 mm. The thickness of the walls may be 0.25 mm, 0.5 mm or 0.75 mm. In addition, the thickness of the walls of the reservoir 5110 may vary throughout the reservoir 5110 as long as the walls are thin enough to allow sufficient transfer of heat to maintain the liquid at a desired temperature.

A reservoir 5110 may comprise a set of conductive portions made of thermally conductive material. The set of conductive portions could be used with a humidifier base 5006 with multiple heater surfaces or portions (as opposed to an exemplary humidifier base 5006 in which the heater only comprises a single heater portion located on a bottom surface of the humidifier base 5006), such that each of the set of conductive portions may engage with a heater surface or portion. In some forms, a humidifier base 5006 may comprise multiple heater surfaces or portions, all of which may engage with one continuous wall of the reservoir 5110 in use.

As discussed previously, the reservoir 5110 may expand upon the addition of water and/or pressurized gas. The expansion of the reservoir 5110 may cause the walls of the reservoir 5110 to engage the walls of the humidifier base 5006. Thus, the expansion of the reservoir 5110 may cause (or improve) thermal engagement between the reservoir 5110 and a heater element (or elements) of the humidifier base 5006.

It is further contemplated that one or more heaters 5158 may be molded at least partially within the walls 5160 of the reservoir 5110 (as shown in FIG. 5T) or secured to an interior surface of the reservoir 5110. In addition, a flexible tape heater 5162 may extend from the air inlet 5118 through the interior of the reservoir 5110 and through the air outlet 5120. It should be noted that the flexible tape heater 5162 may only extend a fraction of the length shown in FIG. 5U (e.g., the flexible tape heater 5162 may terminate before reaching the air outlet 5120). Also, a floating heater 5164 may be provided. The floating heater 5164 may be configured to float on the liquid within the reservoir 5110. Electrical connections (not shown) for the heater could be provided on the humidifier base 5006 by way of a plug and socket or other type of connection.

4.6.2.4 Water Level Indicator

The humidifier reservoir 5110 may comprise a water level indicator 5166 as shown in FIG. 5D-5E. In some forms, the water level indicator 5166 may provide one or more indications to a user such as the patient 1000 or a care giver regarding a quantity of the volume of water in the humidifier reservoir 5110. The one or more indications provided by the water level indicator 5166 may include an indication of a maximum, predetermined volume of water, any portions thereof, such as 25%, 50% or 75% or volumes such as 200 ml, 300 ml or 400 ml.

4.6.3 Humidifier Electrical & Thermal Components

The humidifier 5000 may comprise a number of electrical and/or thermal components such as those listed below.

The reservoir 5110 may comprise an electrical circuit. In one form, the circuit may comprise a substrate that also forms a part of a reservoir wall. The substrate may comprise a flexible polymer film, for example film made from polyester, polyimide, polycarbonate, or polypropylene. Additionally, or alternatively, the substrate may be rigidly configured, such as a metal plate constructed from aluminium or a polymer such as polycarbonate or polypropylene.

The electrical circuit may also comprise conductive ink printed onto the substrate to form electrical track(s). The electrical circuit may further comprise one or more humidifier transducers 5116, which may be surface mounted onto a reservoir wall or otherwise adhered. The electrical circuit may comprise electrically resistive tracks, such as a heating circuit, as will be described in further detail below.

Thus, a wall of the reservoir 5110 (or a part thereof) may form a substrate for a heat generating component such as an electrically resistive heating track and/or for mounting one or more electrical components such as a transducer. Electrical tracks and/or components may be printed, adhered onto, surface mounted, or otherwise coupled with the substrate to create one or more electrical circuits on the reservoir 5110. The one or more electrical circuits may be then electrically connectable to a power supply, such as the humidifier base 5006 or the RPT device 4000.

The reservoir 5110 may thus comprise one or more electrical connectors, each comprising one or more terminals for a power and/or electrical signals (e.g. from a sensor). The one or more electrical connectors may use a wall of the reservoir 5110 as a substrate or comprise an additional component connected thereto, coupled to the heater and/or sensor using any of various known means.

An RPT device 4000 and/or a humidifier base 5006 may thus comprise one or more complementary connectors to couple to and/or receive the one or more connectors of the reservoir 5110.

4.6.3.1 Humidifier Transducer(s)

The humidifier 5000 may comprise one or more humidifier transducers (sensors) 5116 instead of, or in addition to, transducers 4270 described above. Humidifier transducers 5116 may include one or more of an air pressure sensor, an air flow rate transducer, a temperature sensor, or a humidity sensor as shown in FIG. 5D. A humidifier transducer may produce one or more output signals which may be communicated to a controller such as the central controller 4230 and/or a humidifier controller 5176. In some forms, a humidifier transducer may be located externally to the humidifier 5000 (such as in the air circuit 4170) while communicating the output signal to the controller.

The reservoir 5110 may comprise one or more of the humidifier transducers 5116. One or more transducers may be mounted directly onto the reservoir 5110, such as by using a wall of the reservoir 5110 as a substrate onto which an electrical circuit may be printed, adhered to or otherwise located.

4.6.3.1.1 Pressure Transducer

One or more pressure transducers may be provided to the humidifier 5000 in addition to, or instead of, a pressure sensor 4272 provided in the RPT device 4000.

4.6.3.1.2 Flow Rate Transducer

One or more flow rate transducers may be provided to the humidifier 5000 in addition to, or instead of, a flow rate sensor 4274 provided in the RPT device 4000.

4.6.3.1.3 Temperature Transducer

The humidifier 5000 may comprise one or more temperature transducers. The one or more temperature transducers may be configured to measure one or more temperatures such as of the heater 5158 and/or of the flow of air downstream of the humidifier outlet 5004. In some forms, the humidifier 5000 may further comprise a temperature sensor to detect the temperature of the ambient air.

4.6.3.1.4 Humidity Transducer

In one form, the humidifier 5000 may comprise one or more humidity sensors to detect a humidity of a gas, such as the ambient air. The humidity sensor may be placed towards the humidifier outlet 5004 in some forms to measure a humidity of the gas delivered from the humidifier 5000. The humidity sensor may be an absolute humidity sensor or a relative humidity sensor.

4.6.3.2 Heating Element

As discussed above, a heating element (or a heater) may be provided to the humidifier 5000 in some cases to provide a heat input to one or more of the volume of water in the humidifier reservoir 5110 and/or to the flow of air. The heating element may comprise a heat generating component such as an electrically resistive heating track. One suitable example of a heating element is a layered heating element such as one described in the PCT Patent Application Publication No. WO 2012/171072, which is incorporated herewith by reference in its entirety.

In some forms, the heating element may be provided in the humidifier base 5006 where heat may be provided to the humidifier reservoir 5110 primarily by conduction.

The humidifier 5000 may comprise one or more heaters or heating regions in the at least one wall defining the receiving space 5112. A corresponding humidifier reservoir 5110 may be configured such that in use, the one or more heating regions may effectively transfer heat to the reservoir 5110, such as by being engaged thereto.

The heating regions may be disposed within the receiving space 5112. In one example, the at least one wall defining the receiving space 5112 may comprise a bottom wall and four, orthogonal side walls, thus defining a rectangular prism shaped receiving space. In such an arrangement, a heating region may be disposed on the bottom wall of the receiving space 5112. Additionally, or alternatively, heating regions may be disposed in one or more of each side wall defining the receiving space 5112. Furthermore, it will be understood that a single wall may comprise a plurality of heating regions, such as a first heating region above a second heating region. In such a configuration they may be separately controlled.

In some forms, the reservoir 5110 may comprise a heater configured to heat the volume of water contained therein. The reservoir 5110 may comprise one or more heating regions, such as one, two, three, four, five, ten, fifteen or twenty for example, although any other numbers may be suitable. The heating regions may be distributed throughout the reservoir 5110 in some forms such as evenly distributed throughout the reservoir 5110.

Additionally, or alternatively, the heating regions may be distributed throughout the reservoir 5110 such that when in use, a set of heating regions may be disposed towards a bottom wall of the receiving space 5112, and a set of heating regions may be disposed towards one or more of each side wall defining the receiving space 5112.

The reservoir 5110 may comprise a set of heating regions configured to control a temperature at a point of high temperature gradients, such as at an interface between air in the reservoir 5110 and ambient air. For example, the reservoir 5110 may comprise a set of heating regions disposed where the reservoir 5110 may be exposed to the ambient air, such as a top surface (away from the frame 5154) of the reservoir 5110 in a configuration shown in FIG. 5Q.

In one aspect, such interface heating regions may reduce a temperature distribution within the reservoir 5110. Thus, placement of a set of heating regions at an interface between ambient air and air in the reservoir 5110 may advantageously an accurate control of air temperature within the reservoir 5110.

Each of the heating regions may be separately controlled, as described above for example. In some forms, the reservoir 5110 may comprise a first set of heating regions configured to heat a first chamber 5142 and a second set of heating regions configured to heat a second chamber 5144. The first chamber 5142 and the second chamber 5144 may be separated by a backflow prevention system, such as a divider 5140 as shown in FIG. 5L.

Thus, the first set of heating regions may be configured to substantially heat a flow of air in the first chamber 5142 prior to it entering the second chamber 5144, and the second set of heating regions may be configured to heat air flowing through the second chamber 5144 as well as the volume of water contained therein. A potential advantage of such an arrangement may be that the saturation point of the air flow may be increased, allowing the air flow to advantageously contain a higher moisture content therein.

In one form, the first set of heating regions may be configured to deliver an increased power output when a temperature of the volume of water in the reservoir 5110 is low. The increased power output may thereby further pre-heat the air flow before it comes into contact with the volume of water and/or the water vapour (e.g. in the second chamber). One suitable exemplary scenario may be during a start-up phase, where the humidifier 5000 and/or the RPT device 4000 has been activated or switched on recently, and the volume of water has not sufficiently warmed up. Another example may be when an ambient temperature is particularly low, wherein pre-heating the air flow may be beneficial.

Heating requirements for air and water may be different for a number of reasons. For example, the volume of water in a reservoir 5110 is a stationary (or at least slowly changing), fixed, quantity while air flows through the humidifier 5000, at a flow rate of up to approximately 100 L/min. However, the heat capacity of air is lower (approximately ¼) than that of water, and the density of air is approximately $1/1000^{th}$ of that of water. It may therefore require substantially less energy to heat air than it does to heat water. The first set of heating regions may be thus configured to deliver a substantially lower heat output quantity than the second set of heating regions, such as two, five, ten, twenty times lower, while meeting heating requirements for both the air flow as well as the volume of water.

4.6.3.3 Humidifier Controller

According to one arrangement of the present technology, a humidifier 5000 may comprise a humidifier controller 5176 as shown in FIG. 5A. In one form, the humidifier controller 5176 may be a part of the central controller 4230. In another form, the humidifier controller 5176 may be a separate controller, which may be in communication with the central controller 4230.

In one form, the humidifier controller 5176 may receive as inputs measures of characteristics (such as temperature, humidity, pressure and/or flow rate), for example of the flow of air, the water in the reservoir 5110 and/or the humidifier 5000. The humidifier controller 5176 may also be configured to execute or implement humidifier algorithms and/or deliver one or more output signals.

As shown in FIG. 5A, the humidifier controller 5176 may comprise one or more controllers, such as a central humidifier controller 5178, a heated air circuit controller 5180 configured to control the temperature of a heated air circuit 4170 and/or a heating element controller 5182 configured to control the temperature of the base unit heater (not shown).

4.7 GLOSSARY

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.7.2 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$.

4.8 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 REFERENCE SIGNS LIST 1000 patient
1100 bed partner
3000 patient interface
3100 seal-forming structure
3200 plenum chamber
3300 stabilising structure
3400 vent
3600 connection port
3700 forehead support
4000 RPT device
4010 external housing
4012 upper portion
4014 lower portion
4015 panel
4016 chassis
4018 handle
4020 pneumatic block
4100 mechanical and pneumatic components
4110 air filter
4112 inlet air filter
4114 outlet air filter
4122 inlet muffler
4124 outlet muffler
4140 pressure generator
4142 blower
4144 motor
4160 anti-spill back valve
4170 air circuit
4180 supplemental oxygen
4200 electrical components
4202 printed circuit board assembly
4210 power supply
4220 input device
4230 central controller
4232 clock
4240 therapy device controller
4250 protection circuit
4260 memory
4270 transducer
4272 pressure sensor
4274 flow rate sensor
4276 motor speed transducer
4280 data communication interface
4282 remote external communication network
4284 local external communication network
4286 remote external device
4288 local external device
4290 output device
4292 display driver
4294 display
5000 humidifier
5002 humidifier inlet
5004 humidifier outlet
5006 humidifier base
5110 reservoir
5112 receiving space
5114 engaging portion
5116 humidifier transducer or sensor
5118 air inlet
5120 air outlet
5122 main body
5124 connector
5126 connector
5128 top portion
5130 bottom portion
5132 securing mechanism
5134 seal
5136 port
5138 opening
5140 divider
5142 first chamber
5144 second chamber
5146 opening
5148 check valve
5150 rib
5152 exoskeleton
5154 frame
5156 conductive portion
5158 heater
5160 wall
5162 flexible tape heater
5164 floating heater
5166 water level indicator
5167 travel bag
5168 first receptacle
5170 second receptacle
5172 securement strap
5174 third receptacle
5175 securement strap
5176 humidifier controller
5178 central humidifier controller
5180 heated air circuit controller
5182 heating element controller

The invention claimed is:

1. A humidifier configured to humidify a pressurized flow of air to be delivered by way of an air flow path to a patient, the humidifier comprising:
a base unit comprising at least one wall defining a receiving space;
a variable volume reservoir comprising reservoir air inlet configured to form a sealed connection with the air flow path, the variable volume reservoir being configured to hold a body of water and receive the flow of air through the reservoir air inlet to humidify the flow of air for delivery to the patient; and
a heater for heating the body of water,
wherein the receiving space is configured to removably receive the variable volume reservoir and the variable volume reservoir is conformable to a shape of the receiving space.

2. The humidifier of claim 1, wherein the variable volume reservoir is collapsible to a flat plate.

3. The humidifier of claim 1, wherein the at least one wall defines a prism shaped receiving space.

4. The humidifier of claim 1, wherein the variable volume reservoir comprises low thermal impedance material configured to engage the heater in use.

5. The humidifier of claim 4, wherein the low thermal impedance material comprises at least one of polyethylene or polyamide.

6. The humidifier of claim 1, wherein the variable volume reservoir does not comprise a metal plate.

7. The humidifier of claim 1, wherein the variable volume reservoir comprises the heater.

8. The humidifier of claim 7, wherein the heater is a flexible tape heater.

9. The humidifier of claim 8, wherein at least a part of the heater is molded within a wall of the variable volume reservoir.

10. The humidifier of claim 1, wherein the variable volume reservoir comprises a water inlet.

11. The humidifier of claim 10, wherein the reservoir air inlet comprises an ISO standard connector for fluidly connecting to a respiratory apparatus.

12. The humidifier of claim 1, wherein the base unit further comprises a base unit air inlet and a base unit air outlet,
wherein the variable volume reservoir further comprises a reservoir air outlet, and
wherein the reservoir air inlet is configured to receive the flow of air from the base unit air inlet, and the reservoir air outlet is configured to discharge humidified air to the base unit air outlet.

13. The humidifier of claim 1, wherein the variable volume reservoir further comprises a surface configured to support the body of water.

14. The humidifier of claim 1, wherein the air flow path is enclosed.

15. A humidifier configured to receive a pressurized flow of respiratory gas from a respiratory pressure therapy (RPT) apparatus by way of a gas flow path, the humidifier comprising:
a flexible chamber configured to hold a body of water and receive the pressurized flow of respiratory gas from the RPT apparatus to humidify the pressurized flow of respiratory gas; and
a base unit configured to support the flexible chamber, the flexible chamber being configured to conform to a shape of a receiving space of the base unit in use,
wherein the flexible chamber is removable from the gas flow path.

16. The humidifier of claim 15, wherein the flexible chamber is configured to expand during use.

17. The humidifier of claim 15, wherein the flexible chamber comprises a flexible main body.

18. The humidifier of claim 17, wherein the flexible chamber comprises a rigidizing structure for the flexible main body.

19. The humidifier of claim 18, wherein the rigidizing structure is one or more ribs extending along an interior surface of the flexible main body.

20. The humidifier of claim 18, wherein the rigidizing structure is an exoskeleton extending across an outer surface of the flexible main body.

21. The humidifier of claim 15, wherein the base unit comprises a heating element.

22. The humidifier of claim 21, wherein the heating element comprises a plurality of heating regions.

23. The humidifier of claim 22, wherein the flexible chamber is configured to engage each of the plurality of heating regions in use.

24. The humidifier of claim 15, wherein the flexible chamber comprises a gas inlet configured to form a sealed connection with the gas flow path, the flexible chamber being configured to the pressurized flow of respiratory gas from the RPT apparatus through the gas inlet.

25. The humidifier of claim 24, wherein the gas inlet is removable from the gas flow path.

26. A humidifier configured to receive a pressurized flow of respiratory gas from a continuous positive airway pressure (CPAP) apparatus by way of a gas flow path, the humidifier comprising:
a conformable chamber configured to hold a body of water and receive the pressurized flow of respiratory gas from the CPAP apparatus to humidify the pressurized flow of respiratory gas; and
at least one wall defining a receiving space configured to retain the conformable chamber in a fixed position relative to the CPAP apparatus,
wherein the at least one wall of the receiving space is configured to force the conformable chamber into a predetermined shape upon the conformable chamber being received by the receiving space, and
wherein the conformable chamber is removable from the gas flow path.

27. The humidifier of claim 26, wherein the receiving space comprises a heating element configured to engage at least one of the walls of the conformable chamber when the conformable chamber is received by the receiving space.

28. The humidifier of claim 26, wherein the conformable chamber comprises a heating element.

29. The humidifier of claim 26, wherein the conformable chamber comprises an air inlet with a check valve.

30. The humidifier of claim 29, wherein the check valve is configured to open during a treatment session of the CPAP apparatus.

31. The humidifier of claim 26, wherein the conformable chamber comprises a divider that divides the conformable chamber into two subchambers.

32. The humidifier of claim 31, wherein the divider is configured to prevent liquid from flowing through an air inlet of the conformable chamber when the conformable chamber is tilted from an operating configuration.

33. The humidifier of claim 26, wherein the conformable chamber comprises a rigidizing structure to add rigidity to the conformable chamber.

34. The humidifier of claim 33, wherein the rigidizing structure is positioned inside the conformable chamber.

35. The humidifier of claim 33, wherein the rigidizing structure is positioned on an outside surface of the conformable chamber.

36. The humidifier of claim 26, wherein the conformable chamber is pre-filled with water.

37. The humidifier of claim 26, wherein the conformable chamber comprises a gas inlet configured to form a sealed connection with the gas flow path, the conformable chamber being configured to receive the pressurized flow of respiratory gas from the CPAP apparatus through the gas inlet.

38. The humidifier of claim 37, wherein the gas inlet is removable from the gas flow path.

39. A humidifier for a continuous positive airway pressure (CPAP) apparatus, the humidifier comprising:
a flexible chamber configured to hold a body of water and receive pressurized gas from the CPAP apparatus to humidify the pressurized gas, the flexible chamber comprising a rigidizer configured to prevent the flexible chamber from collapsing in on itself,
wherein the flexible chamber is configured to directly couple to the CPAP apparatus.

40. The humidifier of claim 39, wherein the rigidizer is at least one of a rib structure positioned inside the flexible chamber and an exoskeleton structure positioned outside the flexible chamber.

* * * * *